(12) United States Patent
Hanaki et al.

(10) Patent No.: US 6,294,527 B1
(45) Date of Patent: Sep. 25, 2001

(54) CEPHEM COMPOUNDS

(75) Inventors: Hideaki Hanaki, Hiratsuka; Hiroaki Yamazaki, Tokyo; Yoshio Tsuchida, Tokyo; Hideki Sato, Tokyo; Keiichi Hiramatsu, Tokyo; Seiichiro Kawashima, Tokyo, all of (JP)

(73) Assignee: Zenyaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/331,183

(22) PCT Filed: Dec. 25, 1997

(86) PCT No.: PCT/JP97/04818

§ 371 Date: Jul. 20, 1999

§ 102(e) Date: Jul. 20, 1999

(87) PCT Pub. No.: WO98/29416

PCT Pub. Date: Jul. 9, 1998

(30) Foreign Application Priority Data

Dec. 25, 1996 (JP) .................................... 8-346034

(51) Int. Cl.$^7$ ..................... C07D 501/24; A61K 31/546; A61P 31/04
(52) U.S. Cl. .......................... 514/203; 514/205; 540/224; 540/225; 540/226; 540/227
(58) Field of Search .................................. 540/224, 225, 540/226, 227; 514/205, 203

(56) References Cited

FOREIGN PATENT DOCUMENTS 3-264590 * 11/1991 (JP) .
6-135972 * 8/1993 (JP) .

* cited by examiner

Primary Examiner—Mark L. Berch
(74) Attorney, Agent, or Firm—Oblon, Spivak, McClelland, Maier & Neustadt, P.C.

(57) ABSTRACT

An antibacterial compound

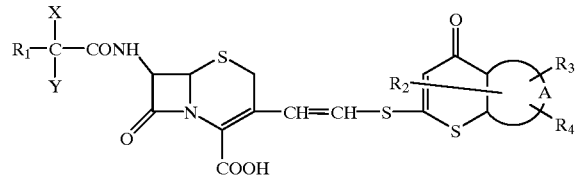

wherein

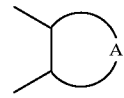

represents benzene ring, pyridine ring, pyrazine ring or 5-membered aromatic neterocycle (having one oxygen or sulfur atom as ring-constituting atom), there being no $R_4$ where

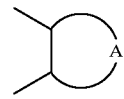

represents 5-membered aromatic heterocycle;

X and Y respectively represent hydrogen atom or CXY represents C=N—OR$_5$ wherein R$_5$ represents hydrogen atom, halo C$_1$–C$_6$ alkyl or C$_3$–C$_7$ cycloalkyl;

R$_1$ represents phenyl, furyl, thienyl, thiazolyl (which may be substituted by amino group), tetrazolyl or thiadiazolyl, R$_2$, R$_3$ and R$_4$ respectively represent hydrogen atom, halogen, hydroxyl group, nitro, C$_1$–C$_6$ alkoxy, trifluoromethyl, isothiuronium C$_1$–C$_6$ alkyl, amino C$_1$–C$_6$ alkyl, halo C$_1$–C$_6$ alkyl, morpholino, piperidino or piperazinyl.

20 Claims, No Drawings

CEPHEM COMPOUNDS

BACKGROUND OF THE INVENTION

TECHNICAL FIELD

1. Field of the Invention

The present invention relates to cephem derivatives or pharmaceutically acceptable salts thereof useful as antibacterial agents and represented by the formula I:

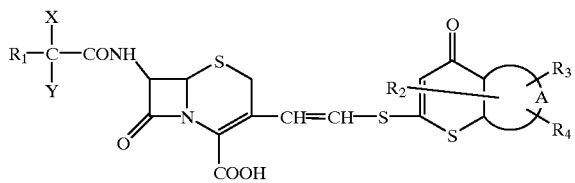

wherein

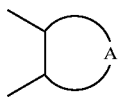

represents benzene ring, pyridine ring, pyrazine ring or 5-membered aromatic heterocycle (having one oxygen or sulfur atom as ring-constituting atom);

X and Y respectively represent hydrogen atom or CXY represents C=N—OR$_5$ wherein R$_5$ represents hydrogen atom, halo C$_1$–C$_6$ alkyl or C$_3$–C$_7$ cycloalkyl;

R$_1$ represents phenyl, furyl, thienyl, thiazolyl (which may be substituted with amino group), tetrazolyl or thiadiazolyl, R$_2$, R$_3$ and R$_4$ respectively represent hydrogen atom, halogen, hydroxyl group, nitro, C$_1$–C$_6$ alkoxy, trifluoromethyl, isothiuronium C$_1$–C$_6$ alkyl, amino C$_1$–C$_6$ alkyl, halo C$_1$–C$_6$ alkyl, morpholino, piperidino or piperazinyl, there being no R$_4$ where

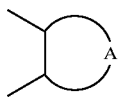

represents 5-membered aromatic heterocycle; or synthetic intermediates of the compounds of the formula I and represented by the formula II

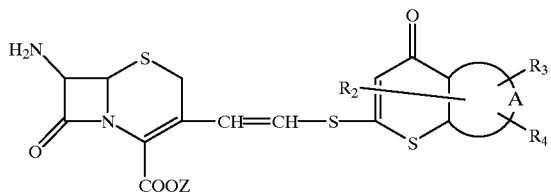

wherein Z represents a protective group for a carboxyl group and

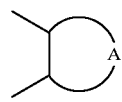

R$_2$, R$_3$ and R$_4$ are as defined above.

2. Description of the Background

In recent years, hardly-curable infections due to pathogenic bacteria having resistance against antibiotics such as methicillin-resistant *Staphylococcus aureus* (MRSA) and vancomycin-resistant enterococci (VRE) have caused serious problems. Vancomycin, which was the only agent against which no resistant bacteria had been found, was frequently used as medicine against MRSA; however, recently, vancomycin-resistant *Staphylococcus aureus* (MU3) was found.

Among the above-mentioned resistant bacteria, MRSA are typical as hospital infecting bacteria and there are MRSA-carriers in healthy humans. Usually, these healthy MRSA-carriers are not sick with MRSA; however, they may tend to become sick with MRSA when they have come into compromised hosts with reduced vital resistance due to operations or other diseases. Once they become sick, a remedy for their sickness is difficult to effect. Nowadays, arbekacin, which is an aminoglycoside, and vancomycin, which is a glycopeptide, are used for such diseases. However, already, there are resistant bacteria against arbekacin; and resistant bacteria such as the above-mentioned MU3 have been found also as to vancomycin only against which there were no resistant bacteria. Such vancomycin-resistant MRSA are found all over Japan so that there is a fear that, in near feature, MRSA infectious diseses will increase which cannot be treated with vancomycin.

Although VRE provide world-shaking issues, though they have not been found in Japan yet. VRE are bacteria which have resistance against various antibacaterial agents just as MRSA and which derive from enterococci (*E. faecalis* and *E. faecium*) against which in turn only vancomycin was effective and which have gained high resistance against vancomycin, too. It is highly feared that, in the future, VRE will appear in Japan or prevail as imported infections. However, no effective medicines are present now and have been developed yet.

Coming of such medical crisis is readily predicted and urgent development of medicines effective for the resistant bacteria is desired to avert such crisis.

Cephem-type antibiotics have been proposed as new antibiotics effective for MRSA. More specifically, cephem derivatives having cyclic ammoniothiovinyl group at the 3-position have been proposed (Japanese Patent Provisional publication (Kokai) Nos. 6-206886 and 7-304779). These compounds are defective both in terms of antibacterial force and toxicity, perhaps, due to the cyclic ammoniothiovinyl group, thus failing to provide new medicines.

DETAILED DESCRIPTION OF THE PREFERRED EMBODIMENTS

The present, the inventors, who made devoted researches to pursue cephem derivatives effective for MRSA and VRE and not having the above-mentioned defective ammonio group in structure, have discovered cephem derivatives of the formula I having at the 3-position thiopyranylthiovinyl group with condensed aromatic ring and having excellent antibacterial activities against MRSA and vancomycin-resistant *E. faecalis,* thus accomplishing the present invention.

Conventionally known 3-thiovinyl cephem derivatives having antibacterial activities are, for example, compounds disclosed in the above-mentioned Publications as well as in Japanese Patent Provisional Publication (Kokai) No. 62-17592 and Japanese Patent Publication (Kokoku) No. 6-39475. There is no disclosure in the publications on compounds having at the 3-position thiopyranylthiovinyl group with condensed aromatic ring, nor disclosed is the fact that they are effective for MRSA and vancomycin-resistant E. faecalis.

The compounds and synthetic intermediates of the present invention are respectively represented by the formulae I and II. The terms used for definition of letters in these formulae will be defined and exemplified in the following.

The term "$C_1$–$C_6$" refers to a group having 1 to 6 carbon atoms.

The term "$C_3$–$C_7$" refers to a group having 3 to 7 carbon atoms.

The "$C_1$–$C_6$ alkyl group" refers to a straight- or branched-chain alkyl group such as methyl, ethyl, n-propyl, isopropyl, n-butyl, tert-butyl, n-pentyl or n-hexyl.

The "$C_3$–$C_7$ cycloalkyl group" refers to cyclic alkyl group such as cyclopropyl, cyclobutyl, cyclopentyl, cyclohexyl or cyclopeptyl.

The "$C_1$–$C_6$ alkoxy group" refers to a straight- or branched-chain alkoxy group such as methoxy, ethoxy, n-propoxy, isopropoxy, n-butoxy, tert-butoxy, n-pentyloxy or n-hexyloxy.

The "isothiuronium $C_1$–$C_6$ alkyl group" refers to the above-mentioned "$C_1$–$C_6$ alkyl group" with isothiuronium group coupled to any of the carbon atoms.

The "amino $C_1$–$C_6$ alkyl group" refers to the above-mentioned "$C_1$–$C_6$ alkyl group" with amino group coupled to any of the carbon atoms.

The "halo $C_1$–$C_6$ alkyl group" refers to the above-mentioned "$C_1$–$C_6$ alkyl group" with halogen atom connected to any of the carbon atoms.

The "halogen atom" may be fluorine, chlorine, bromine or iodine atom.

The "5-membered aromatic heterocycle" may be aromatic 5-membered heterocycle having one oxygen or sulfur atom as ring-constituting atom other than carbon atoms such as furan or thiophene.

When

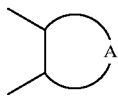

is 5-membered aromatic heterocycle, the thiopyranyl group with condensed ring may be a group with any of the following structures.

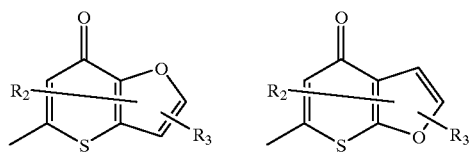

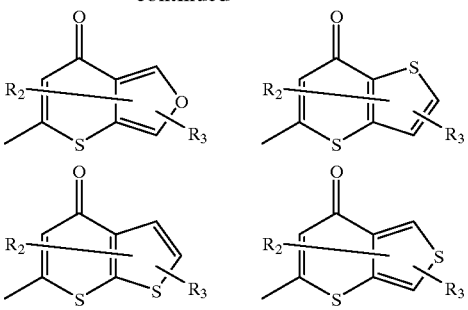

wherein $R_2$ and $R_3$ are as defined above.

The "protective group for the carboxyl group" may be a group which may be ordinarily utilized in the art and which may be readily removed. For example, it may be tri $C_1$–$C_6$ alkylsilyl such as trimethylsilyl, benzhydryl, p-methoxybenzyl, tert-butyl, p-nitrobenzyl.

The compounds according to the present invention may be as follows, though the present invention is not limited to these compounds.

7-[2-(2-Thienyl)acetamido]-3-[2-(4-oxo-4H-1-benzothiopyran-2-yl)thiovinyl]-3-cephem-4-carboxylic acid 7-[2-(2-Thienyl)acetamido]-3-[2-(7-fluoro-4-oxo-4H-1-benzothiopyran-2-yl)thiovinyl]-3-cephem-4-carboxylic acid 7-[2-Cyclopentyloxyimino-2-(2-aminothiazol-4-yl)acetamido]-3-[2-(7-fluoro-4-oxo-4H-1-benzothiopyran-2-yl)thiovinyl]-3-cephem-4-carboxylic acid 7-[2-Fluoromethyloxyimino-2-(2-aminothiazol-4-yl)acetamido]-3-[2-(7-fluoro-4-oxo-4H-1-benzothiopyran-2-yl)thiovinyl]-3-cephem-4-carboxylic acid 7-[2-(2-Thienyl)acetamido]-3-[2-(7-chloro-4-oxo-4H-1-benzothiopyran-2-yl)thiovinyl]-3-cephem-4-carboxylic acid 7-[2-Hydroxyimino-2-(2-aminothiazol-4-yl)acetamido]-3-[2-(7-chloro-4-oxo-4H-1-benzothiopyran-2-yl)thiovinyl]-3-cephem-4-carboxylic acid 7-[2-Cyclopentyloxyimino-2-(2-aminothiazol-4-yl)acetamido]-3-[2-(7-chloro-4-oxo-4H-1-benzothiopyran-2-yl)thiovinyl]-3-cephem-4-carboxylic acid 7-[2-Fluoromethyloxyimino-2-(2-aminothiazol-4-yl)acetamido]-3-[2-(7-chloro-4-oxo-4H-1-benzothiopyran-2-yl)thiovinyl]-3-cephem-4-carboxylic acid 7-[2-(2-Thienyl)acetamido]-3-[2-(7-methoxy-4-oxo-4H-1-benzothiopyran-2-yl)thiovinyl]-3-cephem-4-carboxylic acid 7-[2-Hydroxyimino-2-(2-aminothiazol-4-yl)acetamido]-3-[2-(7-methoxy-4-oxo-4H-1-benzothiopyran-2-yl)thiovinyl]-3-cephem-4-carboxylic acid 7-[2-Cyclopentyloxyimino-2-(2-aminothiazol-4-yl)acetamido]-3-[2-(7-methoxy-4-oxo-4H-1-benzothiopyran-2-yl)thiovinyl]-3-cephem-4-carboxylic acid 7-[2-Fluoromethyloxyimino-2-(2-aminothiazol-4-yl)acetamido]-3-[2-(7-methoxy-4-oxo-4H-1-benzothiopyran-2-yl)thiovinyl]-3-cephem-4-carboxylic acid 7-[2-(2-Thienyl)acetamido]-3-[2-(4-oxo-5-trifluoromethyl-4H-1-benzothiopyran-2-yl)thiovinyl]-3-cephem-4-carboxylic acid 7-[2-Hydroxyimino-2-(2-aminothiazol-4-yl)acetamido]-3-[2-(4-oxo-5-trifluoromethyl-4H-1-benzothiopyran-2-yl)thiovinyl]-3-cephem-4-carboxylic acid 7-[2-Cyclopentyloxyimino-2-(2-aminothiazol-4-yl)
acetamido]-3-[2-(4-oxo-5-trifluoromethyl-4H-1-
benzothiopyran-2-yl)thiovinyl]-3-cephem-4-carboxylic
acid 7-[2-Fluoromethyloxymino-2-(2-aminothiazol-4-yl)
acetamido]-3-[2-(4-oxo-5-trifluoromethyl-4H-1-
benzothiopyran-2-yl)thiovinyl]-3-cephem-4-carboxylic
acid 7-[2-(2-Thienyl)acetamido]-3-[2-(4-oxo-7-trifluoromethyl-
4H-1-benzothiopyran-2-yl)thiovinyl]-3-cephem-4-
carboxylic acid 7-[2-Hydroxyimino-2-(2-aminothiazol-4-yl)acetamido]-3-
[2-(4-oxo-7-trifluoromethyl-4H-1-benzothiopyran-2-yl)
thiovinyl]-3-cephem-4-carboxylic acid 7-[2-Cyclopentyloxytmino-2-(2-aminothiazol-4-yl)
acetamido]-3-[2-(4-oxo-7-trifluoromethyl-4H-1-
benzothiopyran-2-yl)thiovinyl]-3-cephem-4-carboxylic
acid 7-[2-Fluoromethyloxyimino-2-(2-aminothiazol-4-yl)
acetamido]-3-[2-(4-oxo-7-trifluoromethyl-4H-1-
benzothiopyran-2-yl)thiovinyl]-3-cephem-4-carboxylic
acid 7-[2-(2-Thenyl)acetamido]-3-[2-(6,7,8-trifluoro-4-oxo-4H-
1-benzothiopyran-2-yl)thiovinyl]-3-cephem-4-carboxylic
acid 7-[2-Hydroxyimino-2-(2-aminothiazol-4-yl)acetamido]-3-
[2-(6,7,8-trifluoro-4-oxo-4H-1-benzothiopyran-2-yl)
thiovinyl]-3-cephem-4-carboxylic acid 7-[2-Cyclopentyloxyimino-2-(2-aminothiazol-4-yl)
acetamido]-3-[2-(6,7,8-trifluoro-4-oxo-4H-1-
benzothiopyran-2-yl)thiovinyl]-3-cephem-4-carboxylic
acid 7-[2-Fluoromethyloxyimino-2-(2-aminothiazol-4-yl)
acetamido]-3-[2-(6,7,8-trifluoro-4-oxo-4H-1-
benzothiopyran-2-yl)thiovinyl]-3-cephem-4-carboxylic
acid 7-[2-(2-Thienyl)acetamido]-3-[2-(7-hydroxy-4-oxo-4H-1-
benzothiopyran-2-yl)thiovinyl]-3-cephem-4-carboxylic
acid 7-[2-Hydroxyimino-2-(2-aminothiazol-4-yl)acetamido]-3-
[2-(7-hydroxy-4-oxo-4H-1-benzothiopyran-2-yl)
thiovinyl]-3-cephem-4-carboxylic acid 7-[2-Cyclopentyloxyimino-2-(2-aminothiazol-4-yl)
acetamido]-3-[2-(7-hydroxy-4-oxo-4H-1-
benzothiopyran-2-yl)thiovinyl]-3-cephem-4-carboxylic
acid 7-[2-Fluoromethyloxyimino-2-(2-aminothiazol-4-yl)
acetamido]-3-[2-(7-hydroxy-4-oxo-4H-1-
benzothiopyran-2-yl)thiovinyl]-3-cephem-4-carboxylic
acid 7-[2-(2-Thienyl)acetamido]-3-[2-(7-isothiuroniummethyl-
4-oxo-4H-1-benzothiopyran-2-yl)thiovinyl]-3-cephem-4-
carboxylic acid 7-(2-Phenylacetamido)-3-[2-(4-oxo-4H-1-benzothiopyran-
2-yl)thiovinyl]-3-cephem-4-carboxylic acid 7-[2-Hydroxyimino-2-(2-aminothiazol-4-yl)acetamido]-3-
[2-(7-isothiuroniummethyl-4-oxo-4H-1-benzothiopyran-
2-yl)thiovinyl-3-cephem-4-carboxylic acid 7-(2-Phenylacetamido)-3-[2-(7-isothiuroniummethyl-4-
oxo-4H-1-benzothiopyran-2-yl)thiovinyl]-3-cephem-4-
carboxylic acid 7-[2-(2-Thienyl)acetamido]-3-[2-(6,7-
diisothiuroniummethyl-4-oxo-4H-1-benzothiopyran-2-
yl)thiovinyl]-3-3-cephem-4-carboxylic acid 7-[2-Hydroxyimino-2-(2-aminothiazol-4-yl)acetamido]-3-
[2-(6,7-diisothiuroniummethyl-4-oxo-4H-1-
benzothiopyran-2-yl)thiovinyl]-3-cephem-4-carboxylic
acid 7-(2-Phenylacetamido)-3-[2-(6,7-diisothiuroniummethyl-4-
oxo-4H-1-benzothiopyran-2-yl)thiovinyl]-3-cephem-4-
carboxylic acid 7-[2-(2-Thienyl)acetamido]-3-[2-(7-morpholino-4-oxo-4H-
1-benzothiopyran-2-yl)thiovinyl]-3-cephem-4-carboxylic
acid 7-[2-Hydroxyimino-2-(2-aminothiazol-4-yl)acetamido]-3-
[2-(7-morpholino-4-oxo-4H-1-benzothiopyran-2-yl)
thiovinyl]-3-cephem-4-carboxylic acid 7-[2-Cyclopentyloxyimino-2-(2-aminothiazol-4-yl)
acetamido]-3-[2-(7-morpholino-4-oxo-4H-1-
benzothiopyran-2-yl)thiovinyl]-3-cephem-4-carboxylic
acid 7-[2-Fluoromethyloxyimino-2-(2-aminothiazol-4-yl)
acetamido]-3-[2-(7-morpholino-4-oxo-4H-1-
benzothiopyran-2-yl)thiovinyl]-3-cephem-4-carboxylic
acid 7-[2-Hydroxyimino-2-(2-aminothiazol-4-yl)acetamido]-3-
[2-(4-oxo-4H-1-benzothiopyran-2-yl)thiovinyl]-3-
cephem-4-carboxylic acid 7-[2-(1H-Tetrazol-1-yl)acetamido]-3-[2-(4-oxo-4H-1-
benzothiopyran-2-yl)thiovinyl]-3-cephem-4-carboxylic
acid 7-[2-(4-Thiazolyl)acetamido]-3-[2-(4-oxo-4H-1-
benzothiopyran-2-yl)thiovinyl]-3-cephem-4-carboxylic
acid 7-[2-(2-Aminothiazol-4-yl)acetamido]-3-[2-(4-oxo-4H-1-
benzothiopyran-2-yl)thiovinyl]-3-cephem-4-carboxylic
acid 7-[2-Cyclopentyloxyimino-2-(2-aminothiazol-4-yl)
acetamido]-3-[2-(4-oxo-4H-1-benzothiopyran-2-yl)
thiovinyl]-3-cephem-4-carboxylic acid 7-[2-Fluoromethyloxytmino-2-(2-aminothiazol-4-yl)
acetamido]-3-[2-(4-oxo-4H-1-benzothiopyran-2-yl)
thiovinyl]-3-cephem-4-carboxylic acid 7-[2-Hydroxyimino-2-(2-aminothiazol-4-yl)acetamido]-3-
[2-(7-oxo-7H-thiopyrano[3,2-b]furan-5-yl)thiovinyl]-3-
cephem-4-carboxylic acid 7-[2-Hydroxyimino-2-(2-aminothiazol-4-yl)acetamido]-3-
[2-(7-fluoro-4-oxo-4H-1-benzothiopyran-2-yl)thiovinyl]-
3-cephem-4-carboxylic acid 7-[2-(2-Thienyl)acetamido]-3-[2-(4-oxo-7-piperidino-4H-
1-benzothiopyran-2-yl)thiovinyl]-3-cephem-4-carboxylic
acid 7-[2-Hydroxyimino-2-(2-aminothiazol-4-yl)acetamido]-3-
[2-(4-oxo-7-piperidino-4H-1-benzothiopyran-2-yl)
thiovinyl]-3-cephem-4-carboxylic acid 7-[2-Cyclopentyloxyimino-2-(2-aminothiazol-4-yl)
acetamido]-3-[2-(4-oxo-7-piperidino-4H-1-
benzothiopyran-2-yl)thiovinyl]-3-cephem-4-carboxylic
acid 7-[2-Fluoromethyloxyimino-2-(2-aminothiazol-4-yl)
acetamido]-3-[2-(4-oxo-7-piperidino-4H-1-
benzothiopyran-2-yl)thiovinyl]-3-cephem-4-carboxylic
acid 7-[2-(2-Thienyl)acetamido]-3-[2-(7-oxo-7H-thiopyrano[3,
2-b]furan-5-yl)thiovinyl]-3-cephem-4-carboxylic acid 7-[2-Cyclopentyloxyimino-2-(2-aminothiazol-4-yl
)acetamido]-3-[2-(7-oxo-7H-thiopyrano[3,2-b]furan-5-
yl)thiovinyl]-3-cephem-4-carboxylic acid 7-[2-Fluoromethyloxyimino-2-(2-aminothiazol-4-yl)
acetamido]-3-[2-(7-oxo-7H-thiopyrano[3,2-b]furan-5-yl)
thiovinyl]-3-cephem-4-carboxylic acid 7-[2-(2-Thienyl)acetamido]-3-[2-(7-oxo-7H-thieno[3,2-b]
thiopyran-5-yl)thiovinyl]-3-cephem-4-carboxylic acid 7-[2-Hydroxyimino-2-(2-aminothiazol-4-yl)acetamido]-3-
[2-(7-oxo-7H-thieno[3,2-b]thiopyran-5-yl)thiovinyl]-3-
cephem-4-carboxylic acid 7-[2-Cyclopentyloxyimino-2-(2-aminothiazol-4-yl)
acetamido]-3-[2-(7-oxo-7H-thieno[3,2-b]thiopyran-5-yl)
thiovinyl]-3-cephem-4-carboxylic acid 7-[2-Fluoromethyloxyimino-2-(2-aminothiazol-4-yl)
aetamido]-3-[2-(7-oxo-7H-thieno[3,2-b]thiopyran-5-yl)
thiovinyl]-3-cephem-4-carboxylic acid 7-[2-(2-Thienyl)acetamido]-3-[2-(3-nitro-7-oxo-7H-thieno
([3,2-b]thiopyran-5-yl)thiovinyl]-3-cephem-4-carboxylic
acid 7-[2-(2-Thienyl)acetamido]-3-[2-(6-bromo-7-oxo-7H-
thieno[3,2-b]thiopyran-5-yl)thiovinyl]-3-cephem-4-
carboxylic acid 7-[2-(2-Thienyl)acetamido]-3-[2-(6-isothiuroniummethyl-
7-oxo-7H-thieno[3,2-b]thiopyran-5-yl)thiovinyl]-3-
cephem-4-carboxylic acid 7-[2-Hydroxyimino-2-(2-aminothiazol-4-yl)acetamido]-3-
[2-(7-oxo-7H-thieno[3,2-b]thiopyran-5-yl)thiovinyl]-3-
cephem-4-carboxylic acid 7-[2-(2-Thienyl)acetamido]-3-[2-(5-aminomethyl-2-chloro-
4-oxo-4H-thieno[2,3-b]thiopyran-6-yl)thiovinyl]-3-
cephem-4-carboxylic acid 7-(2-Phenylacetamido)-3-[2-(7-oxo-7H-thieno[3,2-b]
thiopyran-5-yl)thiovinyl]-3-cephem-4-carboxylic acid 7-[2-Hydroxyimino-2-(2-aminothiazol-4-yl)acetamido]-3-
[2-(6-bromo-7-oxo-7H-thieno[3,2-b]thiopyran-5-yl)
thiovinyl]-3-cephem-4-carboxylic acid 7-(2-Phenylacetamido)-3-[2-(6-bromo-7-oxo-7H-thieno[3,
2-b]thiopyran-5-yl)thiovinyl]-3-cephem-4-carboxylic
acid 7-[2-Hydroxylmino-2-(2-aminothiazol-4-yl)acetamido]-3-
[2-(3-nitro-7-oxo-7H-thieno[3,2-b]thiopyran-5-yl)
thiovinyl]-3-cephem-4-carboxylic acid 7-(2-Phenylacetamido)-3-[2-(3-nitro-7-oxo-7H-thieno[3,2-
b]thiopyran-5-yl)thiovinyl]-3-cephem-4-carboxylic acid 7-[2-Hydroxyimino-2-(2-aminothiazol-4-yl)acetamido]-3-
[2-(6-isothiuroniummethyl-7-oxo-7H-thieno[3,2-b]
thiopyran-5-yl)thiovinyl]-3-cephem-4-carboxylic acid 7-[2-Hydroxyimino-2-(2-aminothiazol-4-yl)acetamido]-3-
[2-(5-aminomethyl-2-chloro-4-oxo-4H-thieno[2,3-b]
thiopyran-6-yl)thiovinyl]-3-cephem-4-carboxylic acid 7-(2-Phenylacetamido)-3-[2-(5-aminomethyl-2-chloro-4-
oxo-4H-thieno[2,3-b]thiopyran-6-yl)thiovinyl]-3-
cephem-4-carboxylic acid 7-[2-(2-Thienyl)acetamido)-3-[2-[6-(2-aminoethyl)-7-oxo-
7H-thieno[3,2-b]thiopyran-5-yl]thiovinyl]-3-cephem-4-
carboxylic acid 7-[2-Hydroxyimino-2-(2-aminothiazol-4-yl)acetamido]-3-
[2-[6-(2-aminoethyl)-7-oxo-7H-thieno[3,2-b]thiopyran-
5-yl]thiovinyl]-3-cephem-4-carboxylic acid 7-(2-Phenylacetamido)-3-[2-[6-(2-aminoethyl)-7-oxo-7H-
thieno[3,2-b]thiopyran-5-yl]thiovinyl]-3-cephem-4-
carboxylic acid 7-[2-(2-Thienyl)acetamido)-3-[2-(2-chloro-4-oxo-4H-
thieno[2,3-b]thiopyran-6-yl)thiovinyl]-3-cephem-4-
carboxylic acid 7-[2-Hydroxylmino-2-(2-aminothiazol-4-yl)acetamido]-3-
[2-(2-chloro-4-oxo-4H-thieno[2,3-b]thiopyran-6-yl)
thiovinyl]-3-cephem-4-carboxylic acid 7-[2-Cyclopentyloxyimino-2-(2-aminothiazol-4-yl)
acetamido]-3-[2-(2-chloro-4-oxo-4H-thieno[2,3-b]
thiopyran-6-yl)thiovinyl]-3-cephem-4-carboxylic acid 7-[2-Fluoromethyloxyimino-2-(2-aminothiazol-4-yl)
acetamido]-3-[2-(2-chloro-4-oxo-4H-thieno[2,3-b]
thiopyran-6-yl)thiovinyl]-3-cephem-4-carboxylic acid 7-[2-(2-Thienyl)acetamido]-3-[2-(7-oxo-7H-thieno[3,4-b]
thiopyran-5-yl)thiovinyl]-3-cephem-4-carboxylic acid 7-[2-Hydroxyimino-2-(2-aminothiazol-4-yl)acetamido]-3-
[2-(7-oxo-7H-thieno[3,4-b]thiopyran-5-yl)thiovinyl]-3-
cephem-4-carboxylic acid 7-[2-Cyclopentyloxyimino-2-(2-aminothiazol-4-yl)
acetamido]-3-[2-(7-oxo-7H-thieno[3,4-b]thiopyran-5-yl)
thiovinyl]-3-cephem-4-carboxylic acid 7-[2-Fluoromethyloxyimino-2-(2-aminothiazol-4-yl)
acetamido]-3-[2-(7-oxo-7H-thieno[3,4-b]thiopyran-5-yl)
thiovinyl]-3-cephem-4-carboxylic acid 7-[2-(2-Thienyl)acetamido]-3-[2-(7-oxo-7H-thiopyrano[2,
3-c]furan-5-yl)thiovinyl]-3-cephem-4-carboxylic acid 7-[2-Hydroxyimino-2-(2-aminothiazol-4-yl)acetamido]-3-
[2-(7-oxo-7H-thiopyrano[2,3-c]furan-5-yl)thiovinyl]-3-
cephem-4-carboxylic acid 7-[2-Cyclopentyloxyimino-2-(2-aminothiazol-4-yl)
acetamido]-3-[2-(7-oxo-7H-thiopyrano[2,3-c]furan-5-yl)
thiovinyl]-3-cephem-4-carboxylic acid 7-[2-Fluoromethyloxyimino-2-(2-aminothiazol-4-yl)
acetamido]-3-[2-(7-oxo-7H-thiopyrano[2,3-c]furan-5-yl)
thiovinyl]-3-cephem-4-carboxylic acid 7-[2-(2-Thienyl)acetamido]-3-[2-(7-oxo-7H-thiopyrano[2,
3-b]furan-5-yl)thiovinyl]-3-cephem-4-carboxylic acid 7-[2-Hydroxyimino-2-(2-aminothiazol-4-yl)acetamido]-3-
[2-(7-oxo-7H-thiopyrano[2,3-b]furan-5-yl)thiovinyl]-3-
cephem-4-carboxylic acid 7-[2-Cyclopentyloxyimino-2-(2-aminothiazol-4-yl)
acetamido]-3-[2-(7-oxo-7H-thiopyrano[2,3-b]furan-5-yl)
thiovinyl]-3-cephem-4-carboxylic acid 7-[2-Fluoromethyloxyimino-2-(2-aminothiazol-4-yl)
acetamido]-3-[2-(7-oxo-7H-thiopyrano[2,3-b]furan-5-yl)
thiovinyl]-3-cephem-4-carboxylic acid 7-[2-(2-Thienyl)acetamido]-3-[2-(4-oxo-7-(1-piperazinyl-
4H-1-benzothiopyran-2-yl)thiovinyl]-3-cephem-4-
carboxylic acid 7-[2-Hydroxyimino-2-(2-aminothiazol-4-yl)acetamido]-3-
[2-(4-oxo-7-(1-piperazinyl)-4H-1-benzothiopyran-2-yl)
thiovinyl]-3-cephem-4-carboxylic acid 7-[2-Cyclopentyloxyimino-2-(2-aminothiazol-4-yl)
acetamido]-3-[2-(4-oxo-7-(1-piperazinyl)-4H-1-
benzothiopyran-2-yl)thiovinyl]-3-cephem-4-carboxylic
acid 7-[2-Fluoromethyloxyimino-2-(2-aminothiazol-4-yl)
acetamido]-3-[2-(4-oxo-7-(1-piperazinyl)-4H-1-
benzothiopyran-2-yl)thiovinyl]-3-cephem-4-carboxylic
acid 7-[2-(2-Thienyl)acetamido]-3-[2-(4-oxo-4H-thiopyrano[2,
3-b]pyridin-2-yl)thiovinyl]-3-cephem-4-carboxylic acid 7-[2-Hydroxyimino-2-(2-aminothiazol-4-yl)acetamido]-3-
[2-(4-oxo-4H-thiopyrano[2,3-b]pyridin-2-yl)thiovinyl]-
3-cephem-4-carboxylic acid 7-(2-Phenylacetamido)-3-[2-(4-oxo-4H-thiopyrano[2,3-b]
pyridin-2-yl)thiovinyl]-3-cephem-4-carboxylic acid 7-[2-(2-Thienyl)acetamido]-3-[2-(8-oxo-8H-thiopyrano[2,
3-b]pyrazin-6-yl)thiovinyl]-3-cephem-4-carboxylic acid 7-[2-Hydroxyimino-2-(2-aminothiazol-4-yl)acetamido]-3-
[2-(8-oxo-8H-thiopyrano[2,3-b]pyrazin-6-yl)thiovinyl]-
3-cephem-4-carboxylic acid 7-(2-Phenylacetamido)-3-[2-(8-oxo-8H-thiopyrano[2,3-b]
pyrazin-6-yl)thiovinyl]-3-cephem-4-carboxylic acid The compounds of the formula I, which have vinyl group at the 3-position of the structure, may include the following cis isomers (i) and trans isomers (ii), and the respective isomers and their mixtures may be included in the compounds of the invention. The trans isomers are preferable from the viewpoint of antibacterial force.

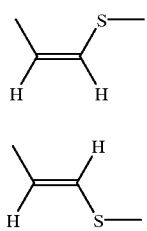

When CXY at the 7-position is an imino group of C=N—OR$_5$ wherein R$_5$ is as defined above, the following syn isomers (iii) and anti isomers (iv) exist, the respective isomers and their mixtures being included in the compounds of the present invention. The syn isomers are preferable from the viewpoint of antibacterial force.

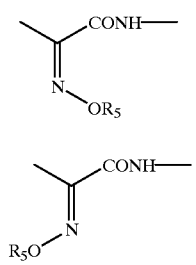

wherein R$_5$ is as defined above.

Moreover, the compounds of the invention may be in the form of pharmaceutically acceptable salts such as alkali salts, organic ammonium salts or acid addition salts. The appropriate alkali salts which can be used include, for example, potassium salt, sodium salt, calcium salt, magnesium salt, barium salt and ammonium salt. The appropriate acid addition salts which can be used include inorganic salts such as hydrochloride, hydrobromide, sulfate, nitrate and phosphate as well as organic acid salts such as acetate, oxalate, propionate, glycolate, lactate, pyruvate, malonate, succinate, maleate, fumarate, malate, tartrate, citrate, benzoate, cinnamate, methanesulfonate, benzenesulfonate, p-toluenesulfonate and salicylate.

The synthetic intermediates of the present invention are, as shown by the formula II, carboxyls which are different from the compounds I of the present invention in that they have cephem with protective group at the 4-position and with amino at the 7-position. However, the latter are identical with the former in the substituted group at the 3-position and configuration of their vinyl groups similarly include cis isomers (i), trans isomers (ii) and their mixtures.

The compounds of the present invention may be prepared by the following procedure.

(1) Preparation of the Synthetic Intermediates of the Present Invention

The synthetic intermediates II of the present invention are obtained by, as shown in process (1) of the below-mentioned reaction formula, reacting a cephem compound of the formula III with a mercaptothiopyran derivative of the formula IV in a solvent and, if needed, in the presence of tertiary amine such as ethyldiisopropylamine, triethylamine or pyridin, separating the obtained reaction product, and removing the protective group for the amino group according to a usual manner in the presence of acid such as hydrochloric, formic or p-toluenesulfonic acid.

There is no particular limitation on the solvent employed, providing that it is not involved with the reaction. For example, tetrahydrofuran, dichloromethane, benzene, ethyl acetate, dimethylformamide, hexamethyl phosphoric triamide, dimethyl sulfoxide, acetone or mixture thereof may be used. Alternatively, the above-mentioned tertiary amine itself may be used as the solvent. The aimed intermediates are obtained by reacting the 1–5 moles of the compound of the formula IV per mole of the compound of the formula III at the temperature range of ice cooling to room temperature for 1–6 hours.

(2) Preparation of the Comounds of the Present Invention

The compounds I of the present invention are obtained by, as shown in process (2) of the below-mentioned reaction formula, reacting the synthetic intermediate of the formula II according to the present invention with a compound of the formula V in a solvent, separating the obtained reaction product, and removing the protective group for the carboxyl group according to a usual manner in the presence of hydrochloric acid, aluminium chloride, formic acid, trifluoroacetic acid or p-toluenesulfonic acid. When trifluoroacetic acid is to be used for removal of the protective group, it is preferably reacted in the presence of anisole, thioanisole or phenol so as to facilitate the reaction and suppress any side reactions.

There is no particular limitation on the solvent employed, providing that it is not involved with the reaction. For example, tetrahydrofuran, dichloromethane, chloroform, benzene, ethyl acetate, dimethylformamide, acetone or mixture thereof may be used. The aimed compound is obtained by reacting 1–3 moles of the compound of the formula V per mole of the compound of the formula II at the temperature range of ice cooling to room temperature for 1–6 hours.

[Reaction Scheme]

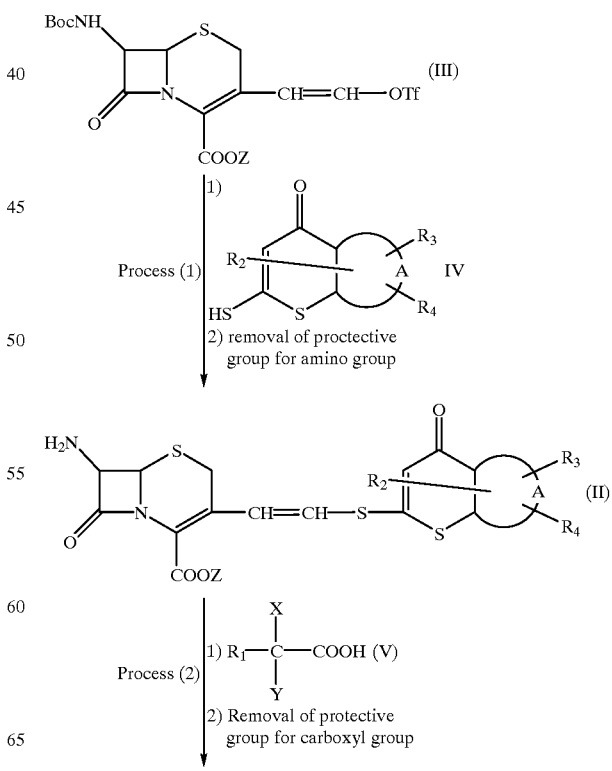

-continued

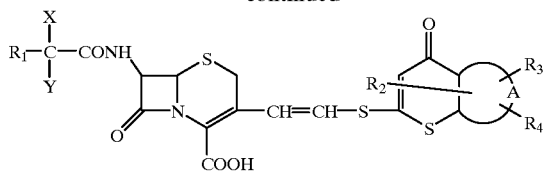

wherein Boc represents tert-butoxycarbonyl and Tf represents trifluoromethansulfonyl,

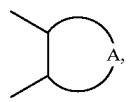

$R_1$, $R_2$, $R_3$, $R_4$, X, Y and Z are as defined above.

Before introduction, the substituted group of the thiopyran compound of the formula IV may be reacted with the cephem compound of the formula III as needs demand.

The sequence of the processes in the above-mentioned Reaction Scheme may be varied. For example, the protective group for the amino group is removed from the compound of the formula III; then, the latter is reacted with the compound of the formula V and further with the compound of the formula IV. Finally, the protective group for the carboxyl group is removed from the reaction product, thus producing the compounds of the present invention.

Thus obtained compounds of the present invention may be separated and purified as needs demand, according to an ordinary method such as extraction, condensation, neutralization, filtration, recrystallization or column chromatography.

Pharamaceutically acceptable salts of the compounds of the present invention may be prepared by various methods known in the art concerned.

Cephem compounds of the formula III which are the starting materials in the above-mentioned processes are known compounds. Mercaptothiopyran derivatives of the formula IV which involve novel materials can be readily prepared substantially in accordance with the processes disclosed in Aust. J. Chem. 40, 1179–1190 (1987), Tetrahedron 35, 551–556 (1979), Japanese Patent Provisional Publication (Kokai) No. 8-73304 or EP 481441.

Next, antibacterial activity of the compounds of the formula I according to the present invention will be described. The numbers of test compounds in this antibacterial test correspond to those in Examples referred to hereinafter.

Antibacterial test was performed in substantial accordance with agar plate dilution method based on Standard method of The Japan Society of Chemotherapy to determine minimum inhibitory concentration (MIC) of the respective test compounds against *Staphylococcus aureus* (*S. aureus* FDA 209P) and vancomycin-resistant enterococci (*E. faecalis* NCTC-12201). Also determined was $MIC_{80}$ on clinically separated strains (27 strains) of MRSA. The inoculated amount was $10^6$ CFU/ml and flomoxef (FMOX) and vancomycin (VCM) were used as controls.

The results are as shown in Table 1.

TABLE 1

| | MIC (μg/ml) | | |
|---|---|---|---|
| tested compound | S. aureus FDA 209P | E. faecalis NCTC-12201 | MRSA $MIC_{80}$ |
| compound 1 | 0.20 | 3.13 | 3.13 |
| compound 2 | 0.05 | 0.78 | 1.56 |
| compound 4 | 0.10 | 1.56 | 3.13 |
| compound 5 | 0.05 | 1.56 | 6.25 |
| compound 7 | 0.025 | 0.78 | 3.13 |
| compound 8 | 0.20 | 12.5 | 6.25 |
| compound 9 | 0.025 | 3.13 | 3.13 |
| compound 10 | 0.05 | 6.25 | 6.25 |
| compound 11 | 0.10 | 1.56 | 3.13 |
| compound 17 | 0.39 | 6.25 | 3.13 |
| compound 18 | 0.39 | 6.25 | 3.13 |
| compound 19 | 0.10 | 3.13 | 3.13 |
| compound 20 | 0.025 | 1.56 | 0.78 |
| compound 21 | 0.025 | 1.56 | 0.78 |
| compound 22 | ≦0.006 | 6.25 | 3.13 |
| compound 23 | 0.10 | 3.13 | 1.56 |
| compound 24 | ≦0.006 | 3.13 | 1.56 |
| compound 25 | 0.013 | 0.78 | 0.78 |
| compound 26 | 0.025 | 1.56 | 1.56 |
| compound 27 | 0.025 | 3.13 | 1.56 |
| compound 28 | 0.0254 | 6.25 | 3.13 |
| compound 30 | ≦0.006 | 6.25 | 3.13 |
| compound 31 | 0.10 | 3.13 | 1.56 |
| FMOX | 0.20 | >100 | 100 |
| VCM | 0.78 | >1000 | 1.56 |

As is clear from the above, the compounds of the present invention of the formula I are effective for MRSA and vancomycin-resistant *E. faecalis* and can be applied for treatment of infections caused by MRSA or other pathogenic bacteria. The compounds of the present invention may be administered to human or mammal orally or parenterally. In oral administration, the compounds may be in the form of tablets, coated tablets, powders, granules, capsules, microcapsules, syrups and the like; and in parenteral administration, in the form of injections which may include soluble freeze-drying form, suppositories and the like. In the preparation of these forms, pharmaceutically acceptable excipient, binders, lubricants, disintegrators, suspensions, emulsifiers, antiseptics, isotonics, stabilizers and dispersing agents, for example, lactose, sucrose, starch, dextrin, crystalline cellulose, kaolin, calcium carbonate, talc, magnesium stearate, distilled water, physiological saline solution and amino acid infusion may be used.

The dosage for humans may depend on the condition of the disease to be treated, the age and weight of the patient and the like. A daily dosage for an adult may be in the range of from 100 to 5,000 mg and may be given in divided doses 1 to 4 times a day.

BEST MODE FOR CARRYING OUT THE INVENTION

The present invention is more specifically illustrated with reference to the following preparations and examples. It is to be, however, noted that the present invention is not limited to these. Unless otherwise recited, the compounds of the present invention and their synthetic intermediates shown in the preparations and examples have vinyl group at the 3-position of cephem as trans isomer.

Preparation 1: Preparation of 2-mercapto-7-methoxy-4-oxo-4H-1-benzothiopyran

In accordance with the process disclosed in Aust. J. Chem. 40, 1179 (1987), the mixture of 2-fluoro-4- methoxyacetophenone (3 g, 22.73 mmol), N,N-dimethylformamide (25 ml), benzene (17.5 ml) and carbon disulfide (3.78 g, 50.01 mmol) was stirred and added with 55% sodium hydride (2.42 g, 55.47 mmol) over about 2.5 hours while inner temperature was maintained at 15–20° C. After additional stirring for 30 minutes, the reaction mixture was added with methanol (0.5 ml) and further stirred for 15 minutes. Benzene was removed under heating to increase inner temperature up to 125–130° C.; at that temperature range, the mixture was heated for 45 minutes and was allowed to cool to room temperature. The reaction mixture was added with water (80 ml) and acetic acid (2.5 ml) and extracted with ether (50 ml×2 times); water layer was filtered out and acidified with concentrated hydrochloric acid. The resulting precipitates were collected by filteration and were recrystallized from methanol-1,2-dichloroethane (1:1) to obtain 3.8 g (yield: 75%) of the titled compound.

Melting Point: 199–200° C.

MS m/z: 224($M^+$)

NMR(DMSO-$d_6$) δ: 3.81(3H, s), 6.97(1H, s), 7.07(1H, dd, J=2.6 Hz, 9.2 Hz), 7.20(1H, d, J=2.6 Hz), 8.04(1H, d, J=9.2 Hz)

Starting from the corresponding starting materials, the following compounds are obtained in accordance with the procedure of the Preparation 1.

6,7,8-Trifluoro-2-mercapto-4-oxo-4H-1-benzothiopyran

Melting Point: 158–161° C.

MS m/z: 248($M^+$)

NMR(DMSO-$d_6$) δ: 7.07(1H, s), 8.03–8.12(1H, m)

2-Mercapto-7-(trifluoromethyl)-4-oxo-4H-1-benzothiopyran

Melting Point: 166–169° C.

MS m/z: 262($M^+$)

NMR(CD$_3$OD) δ: 7.06(1H, s), 7.64(1H, dd, J=1.6 Hz, 8.5 Hz), 7.77(1H, d, J=1.6 Hz), 8.28(1H, d, J=8.5 Hz)

6-Mercapto-8-oxo-8H-thiopyrano[2,3-b]pyrazin

Melting Point: >178° C. (decomp.)

NMR(DMSO-$d_6$) δ: 7.31(1H, br), 8.81(2H, br)

Preparation 2: Preparation of 5-mercapto-7-oxo-7H-thiopyrano-[3,2-b]furan (1) In accordance with the process disclosed in Tetrahedron, 35, 551 (1979), 2-acetyl-3-bromofuran (10.0 g, 53.2 mmol) and carbon disulfide (7.0 g, 93.2 mmol) were dissolved in anhydrous dimethylformamide (70 ml) and the solution was added with 55% sodium hydride (4.0 g, 93.2 mmol) over about 1.5 hours while it was stirred and inner temperature was maintained below 10° C. under ice cooling. After further stirring for 0.5 hour at the temperature, the solution was added with methanol (1.1 ml, 26.6 mmol) and further stirred at room teperature for 40 minutes. Then, the solution was heated and stirred in the boiling water bath for 1 hour and allowed to cool to room temperature. Under water cooling, the solution was added dropwise with methyl iodide (22.6 g, 159.6 mmol) and stirred at room temperature for 24 hours. The solution was injected into ice water, extracted with dichloromethane (300 ml×2 times), washed with water and dried over anhydrous magnesium sulfate. The solvent was removed under reduced pressure and the residue was recrystallized from ethanol using active carbon to obtain 5.9 g (yield: 56%) of 5-methylthio-7-oxo-7H-thiopyrano [3,2-b]furan as colorless needles.

Melting Point: 149–150° C.

NMR(CDCl$_3$) δ: 2.63(3H, s), 6.74(1H, d, J=2.0 Hz), 7.01(1H, s), 7.80(1H, d, J=2.0 Hz)

(2) The obtained compound (5.7 g, 29 mmol) was dissolved in dichloromethane and added dropwise with 80% dichloromethane solution (150 ml) of metachloroperbenzoic acid (5.9 g, 27 mmol) under ice-water cooling and over about 45 minutes. After further stirring at the temperature for one hour, the precipitates were collected by filtration, washed with dichloromethane and dried over air. This solid was stirred for a while in the aqueous solution (100 ml) of diluted sodium hydrogencarbonate and collected by filtration, washed with water and acetone, successively, to obtain 3.3 g (yield: 53%) of 5-methylsulfinyl-7-oxo-7H-thiopyrano[3,2-b]furan as colorless powder.

Melting Point: 230–232° C.

NMR(DMSO-$d_6$) δ: 2.99(3H, s), 7.35(1H, d, J=2.0 Hz), 7.46(1H, s), 8.40(1H, d, J=2.0 Hz)

(3) The obtained compound (3.3 g, 15 mmol) was dissolved in tetrahydrofuran (160 ml), added with about 70% sodium hydrogensulfide (10 g) and stirred at room temperature for 24 hours. The solvent was removed under reduced pressure, added with water (150 ml) for dissolution and washed with dichloromethane. The water layer was acidified with 2N hydrochloric acid under cooling into pH 1–2. The precipitates were collected by filtration and washed with water and ether, successively, to obtain 2.3 g (yield: 82%) of the titled compound as yellow-red powder.

Melting Point: >245° C.

NMR(DMSO-$d_6$) δ: 7.05 and 7.07(2H, m), 8.31(1H, d, J=1.65 Hz)

The following compounds were obtained from the corresponding starting materials and in a procedure similar to that of the Preparation 2.

5-Mercapto-7-oxo-7H-thieno[3,2-b]thiopyran

Melting Point: 151–153° C.

NMR(DMSO-$d_6$) δ: 7.03(1H, s), 7.45(1H, d, J=5.3 Hz), 8.24(1H, d, J=5.3 Hz)

2-Chloro-6-mercapto-4-oxo-4H-thieno[2,3-b]thiopyran

Melting Point: >245° C.

NMR(DMSO-$d_6$) δ: 7.00(1H, s), 7.51(1H, s)

2-Mercapto-4-oxo-4H-thiopyrano[2,3-b]pyridin

Melting Point: 187–190° C. (decomp.)

NMR(DMSO-$d_6$) δ: 7.13(1H, s), 7.55(1H, dd, J=4.6 Hz, 8.2 Hz), 8.47(1H, dd, J=1.7 Hz, 8.2 Hz), 8.76(1H, dd, J=1.7 Hz, 4.6 Hz)

Preparation 3: Preparation of 7-hydroxy-2-mercapto-4-oxo-4H-1-benzothiopyran (1) 7-Methoxy-2-mercapto-4-oxo-4H-1-benzothiopyran (2.00 g, 8.92 mmol) was dissolved in DMF (15 ml) and gradually added with sodium hydride (505.8 mg, 11.59 mmol) over 30 minutes in the ice bath and under nitrogen atmosphere. After removal of the ice bath and stir for 12 hours, the solution was added with methyl iodide (0.83 ml, 13.37 mmol) and further stirred for 3 hours. The reaction liquid was injected into the cooled aqueous solution (100 ml) of saturated ammonium chloride. The precipitated crude crystals were filtrated and fully washed with water and dried in a desiccator under reduced pressure. The crude crystals were washed with the ether-hexane solution to obtain 1.77 g (yield: 83%) of 7-methoxy-2-methylthio-4-oxo-4H-1-benzothiopyran as light yellow powder.
Melting Point: 133–135° C.
NMR(CDCl$_3$) δ: 2.61(3H, s), 3.89(3H, s), 6.82(1H, s), 6.91(1H, d, J=2.6 Hz), 7.65(1H, dd, J=2.6 Hz, 8.9 Hz), 8.38(1H, d, J=8.9 Hz)

(2) The obtained compound (570 mg, 2.39 mmol) was added with hydrobromic acid (20 ml) and refluxed in heating for 28 hours. After allowed to cool, the solution was neutralized with the aqueous solution of 20% sodium hydroxide under cooling in the ice bath. The precipitated crude crystals were filtrated and fully washed with water and dried in a desiccator under reduced pressur. The crude crystals were washed with ether to obtain 520 mg (yield: 97%) of 7-hydroxy-2-methylthio-4-oxo-4H-1-benzothiopyran as light purple powder.
Melting Point: 231–232° C.
NMR(DMSO-d$_6$) δ: 2.69(3H, s), 6.74(1H, s), 7.01(1H, d, J=2.3 Hz), 7.05(1H, brs), 8.16(1H, d, J=8.6 Hz), 10.77(1H, s)

(3) The obtained compound (540 mg, 2.40 mmol) and metachloroperbenzoic acid (860 mg, 3.75 mmol) were used to conduct the process similar to that shown in (2) of the Preparation 2, thus obtaining 559 mg (yield: 97%) of 7-hydroxy-2-methylsulfinyl-4-oxo-4H-1-benzothiopyran as yellow powder.
NMR(DMSO-d$_6$) δ: 3.08(3H, s), 7.18(1H, dd, J=2.3 Hz, 8.9 Hz), 7.27(1H, d, J=2.3 Hz), 7.33(1H, d, J=2.3 Hz), 8.29(1H, d, J=8.9 Hz), 11.02(1H, brs)

(4) The obtained compound (559 mg, 2.32 mmol) and sodium hydrogensulfide (1.05 g, 13.12 mmol) were used to conduct the process similar to that shown in (3) of the Preparation 2, thus obtaining 324 mg (yield: 66%) of the titled compound as yellow powder.
Melting Point: 160–163° C.
NMR(DMSO-d$_6$) δ: 7.01–7.07(3H, m), 8.11(1H, d, J=8.6 Hz), 10.91(1H, br)

Preparation 4: Preparation of 2-mercapto-7-morpholino-4-oxo-4H-1-benzothiopyran (1) 7-Fluoro-2-mercapto-4-oxo-4H-1-benzothiopyran(2.12 g, 10.0 mmol), sodium hydride (567.2 mg, 13.0 mmol) and methyl iodide (0.93 ml, 15.0 mmol) were used to conduct the process simiar to (1) of the Preparation 3, thus obtaining 1.40 g (yield: 62%) of 7-fluoro-2-methylthio-4-oxo-4H-1-benzothiopyran as light yellow powder.
Melting Point: 120–121° C.
NMR(CDCl$_3$) δ: 2.63(3H, s), 6.83(1H, s), 7.18–7.24(2H, m), 8.48(1H, dd, J=5.9 Hz, 9.6 Hz)

(2) The obtained compound (800 mg, 3.53 mmol) was dissolved in pyridine (15 ml), added with morpholine (1.54 ml, 17.67 mmol) and 1,8-diazabicyclo[5,4,0]-7-undecene (DBU) (2.57 ml, 17.67 mmol) and refluxed under heating for 15 hours. The solvent was removed and the residue was purified by column chromatography [silica gel, methylene chloride-methanol (20:1)] to obtain 815 mg (yield: 78%) of 2-methylthio-7-morpholino-4-oxo-4H-1-benzothiopyran as orange powder.
Melting Point: 163–166° C.
NMR(CDCl$_3$) δ: 2.63(3H, s), 3.32(4H, t, J=4.9 Hz), 3.87(4H, t, J=4.9 Hz), 6.76(2H, brs), 7.03(1H, dd, J=2.6 Hz, 9.2 Hz), 8.32(1H, d, J=9.2 Hz)

(3) The obtained compound (815 mg, 2.78 mmol) and metachloroperbenzoic acid (659 mg, 3.05 mmol) were used to conduct the process similar to that shown in (2) of the Preparation 2, thus obtaining 546 mg (yield: 53%) of 2-methylsulfinyl-7-morpholino-4-oxo-4H-1-benzothiopyran as yellow powder.
Melting Point: 198–200° C.
NMR(CDCl$_3$) δ: 2.94(3H, s), 3.37(4H, t, J=4.9 Hz), 3.88(4H, t, J=4.9 Hz), 6.91(1H, d, J=2.6 Hz), 7.10(1H, dd, J=2.3 Hz, 9.2 Hz), 7.17(1H, s), 8.37(1H, d, J=9.2 Hz)

(4) The obtained compound (500 mg, 1.62 mmol) and sodium hydrogensulfide (622 mg, 8.08 mmol) were used to conduct the process similar to that shown in (3) of the Preparation 2, thus obtaining 443 mg (yield: 69%) of the titled compound as yellow powder.
Melting Point: >250° C.
NMR(DMSO-d$_6$) δ: 2.44(4H, t, J=5.3 Hz), 3.66(4H, t, J=5.3 Hz), 6.89(1H, s), 6.99(1H, d, J=2.6 Hz), 7.11(1H, dd, J=2.6 Hz, 9.2 Hz), 7.92(1H, d, J=9.2 Hz)

The following compounds were obtained from the corresponding starting materials and in the prcedure similar to that shown in the Preparation 4.

2-Mercapto-4-oxo-7-piperidino-4H-1-benzothiopyran

Melting Point: 120–122° C.
NMR(DMSO-d$_6$) δ: 1.60(6H, brs), 3.44(4H, brs), 6.93 (1H, s), 7.02(1H, d, J=2.6 Hz), 7.15(1H, dd, J=2.6 Hz, 9.2 Hz), 7.95(1H, d, J=9.2 Hz)

2-Mercapto-7-(4-benzyloxycarbonylpiperazin-1-yl)-4-oxo-4H-1-benzothiopyran

Melting Point: 128–131° C.
NMR(DMSO-d$_6$) δ: 3.55(4H, brs), 3.62(4H, brs), 5.20 (2H, s), 7.04(1H, s), 7.13(1H, d, J=2.3 Hz), 7.24(1H, dd, J=2.3 Hz, 8.9 Hz), 7. 46(5H, brs), 8.07(1H, d, J=8.9 Hz)

Preparation 5: Preparation of 7-hydroxymethyl-2-mercapto-4-oxo-4H-1-benzothiopyran (1) 7-Trifluoromethyl-2-methylthio-4-oxo-4H-1-benzothiopyran (4 g, 14.48 mmol) was added to concentrated sulfuric acid (60 ml) and stirred under heating at 110–120° C. for 20 hours. The reaction mixture was injected to ice water and the precipitates were collected by filtration, dissolved in methyl cellosolve (200 ml) under heating and bleached and purified by active carbon. Then, the solvent was removed under reduced pressure to obtain 1.8 g (yield: 50%) of 7-carboxy-2-methylthio-4-oxo-4H-1-benzothiopyran as Chinese yellow powder.
MS m/z: 252(M$^+$)
NMR(DMSO-d$_6$) δ: 2.72(3H, s), 6.88(1H, s), 8.04(1H, dd, J=1.3 Hz, 8.5 Hz), 8.28(1H, d, J=1.3 Hz), 8.36(1H, d, J=8.5 Hz)

(2) 7-Carboxy-2-methylthio-4-oxo-4H-1-benzothiopyran (1.48 g, 5.87 mmol) was suspended in tetrahydrofuran (30 ml), added with triethylamine (1 ml, 7.17 mmol) and cooled to −10° C. Then, the reaction mixture was added dropwise with ethyl chlorocarbonate (0.6 ml, 5.94 mmol) and stirred at 0–5° C. for 0.5 hour. The reaction mixture was filtered and the insoluble matter was further washed with tetrahydrofuran (10 ml×2 times). The washing liquid was mixed with the previous tetrahydrofuran solution. Sodium borohidride (568 mg, 15 mmol) was suspended in water (8 ml) and added dropwise with the previously obtained tetrahydrofuran solution over 45 minutes under ice-water cooling. The reaction mixture was acidified with 2N hydrochloric acid and extracted by ethyl acetate (300 ml), washed with saturated saline solution and dried over anhydrous magnesium sulfate. The solvent was removed under reduced pressure and the residue was washed with ether to obtain 800mg (yield: 57%) of substaintially pure 7-hydroxymethyl-2-methylthio-4-oxo-4H-1-benzothiopyran.

NMR(CDCl$_3$) δ: 2.62(3H, s), 4.81(1H, d, J=5.6 Hz), 6.83(1H, s), 7.41(1H, d, J=8.3 Hz), 7.52(1H, s), 8.37(1H, d, J=8.3 Hz)

(3) The obtained compound (800 mg, 3.36 mmol) and metachloroperbenzoic acid (725 mg, 3.36 mmol) were used to conduct the process similar to that shown in (2) of the Preparation 2, thus obtaining 660 mg (yield: 77.3%) of 7-hydroxymethyl-2-methylsulfinyl-4-oxo-4H-1-benzothiopyran.

NMR(CDCl$_3$) δ: 2.95(3H, s), 4.87(1H, d, J=4.0 Hz), 7.26(1H, s), 7.53(1H, d, J=8.0 Hz), 7.72(1H, s), 8.47(1H, d, J=8.0 Hz)

(4) The obtained compound (660 mg, 2.6 mmol) and sodium hydrogensulfide (1.6 g, 20.8 mmol) were used to conduct the process similar to that shown in (3) of the Preparation 2, thus obtaining 420 mg (yield: 56%) of the titled compound as yellow powder.

Melting Point: >174° C. (decomp.)

NMR(DMSO-d$_6$) δ: 4.62(2H, s), 7.12(1H, s), 7.47(1H, d, J=8.3 Hz), 7.55(1H, s), 8.14(1H, d, J=8.3 Hz)

Preparation 6: Preparation of 5-tert-butoxycarbonylamino-methyl-2-chloro-6-mercapto-4-oxo-4H-thieno-[2,3-b]thiopyran (1) 2-Chloro-6-methylthio-4-oxo-4H-thieno[2,3-b]thiopyran (6.64 g, 0.027 mol), diethylamine hydrochloride (19.65 g, 0.24 mol) and paraformaldehyde (17.16 g) were added to an aqueous solution of 80% acetic acid and refluxed under heating for 30 hours. The solvent was removed under reduced pressure. The residue was added with ice water and stirred for a while, and supernatant was removed. The remaining viscous matter was dissolved in dimethylformamide (150 ml), filtered for removal of the insoluble matter. Then, the filtrate was added with water (40 ml), methanol (100 ml) and potassium carbonate (37 g, 0.7 mol) and stirred for 35 minutes. Then, ice water (700 ml) was added and the resulting precipitates were collected by filtration. The precipitates were recrystallized from ethanol to obtain 3.5 g (yield: 46.5%) of 2-chloro-5-hydroxymethyl-6-methylthio-4-oxo-4H-thieno[2,3-b]thiopyran.

MS m/z: 278(M$^+$)

(2) The obtained compound (2 g, 7.17 mmol) was dissolved in dichloromethane (30 ml), added with triethylamine (2 ml, 14.34 mmol) under ice cooling, and added dropwise with methanesulfonyl chloride (0.89 ml, 11.47 mmol). The cooling bath was removed and the reaction mixture was stirred at room temperature for 25 hours and added with dichloromethane (150 ml). The reaction mixture was washed with water (50 ml) and dried over anhydrous magnesium sulfate. The solvent was removed under reduced pressure and the residue was washed with ether to obtain 2 g (yield: 94%) of 2-chloro-5-chloromethyl-6-methylthio-4-oxo-4H-thieno[2,3-b]thiopyran.

MS m/z: 296(M$^+$)

NMR(CDCl$_3$) δ: 2.69(3H, s), 4.88(2H, s), 7.54(1H, s)

(3) The obtained compound (2 g, 6.73 mmol) was suspended in dimethylformamide (40 ml), added with sodium azide (1.31 g, 20.19 mmol) while stirred at room temperature, and further stirred for 3 hours. The reaction mixture was added with ice water and the resulting precipitates were recovered by filtration and washed with water to obtain 1.9 g (yield: 93%) of 5-azidomethyl-2-chloro-6-methylthio-4-oxo-4H-thieno[2,3-b]thiopyran.

MS m/z: 303(M$^+$)

IR (KBr): 2093 (–N$_3$) cm$^{-1}$

NMR (CDCl$_3$) δ: 2.66(3H, s), 4.62(2H, s), 7.55(1H, s)

(4) The obtained compound (1.48 g, 4.87 mmol) was dissolved in tetrahydrofuran (40 ml), added with triphenylphosphine (2 g, 7.78 mmol) and water (0.4 ml), successively, and stirred at room temperature for 24 hours. Then, the reaction mixture was added with di-tert-butyldicarbonate (1.7 g, 7.79 mmol) and further stirred at room temperature for 24 hours. Then, the reaction mixture was added with dichloromethane (150 ml), washed with water and dried over anhydrous magnesium sulfate. The solvent was removed under reduced pressure and the residue was purified by silica gel column chromatography (Wako Gel™ C-200: dichloromethane-ethyl acetate=8:1) to obtain 1.5 g (yield: 82%) of 5-tert-butoxycarbonylaminomethyl-2-chloro-6-methylthio-4-oxo-4H-thieno[2,3-b]thiopyran.

MS m/z: 377(M$^+$)

(5) The obtained compound (500 mg, 1.32 mmol) and metachloroperbenzoic acid (299 mg, 1.39 mmol) were used to conduct the process similar to that shown in (2) of the Preparation 2, thus obtaining 450 mg (yield: 87%) of 5-tert-butoxycarbonylaminomethyl-2-chloro-6-methylsulfinyl-4-oxo-4H-thieno[2,3-b]thiopyran. Then, this compound (400 mg, 1.02 mmol) and sodium hydrogensulfide (163 mg, 2.1 mmol) were used to conduct the process similar to that shown in (3) of the Preparation 2, thus obtaining 320 mg (yield: 95%) of the titled compound as yellow powder.

Melting Point: 128–131° C. (decomp.)

NMR(DMSO-d$_6$) δ: 1.40(9H, s), 4.48(2H, s), 7.53(1H, s)

Preparation 7: Preparation of sodium salt of 5-mercapto-7-oxo-6-(2-tetrahydropyranyl)oxymethyl-7H-thieno[3,2-b]thiopyran (1) 5-Methylthio-7-oxo-7H-thieno-[3,2-b]thiopyran (1.77 g, 8.24 mmol) and dimethylamine hydrochloride (6.05 g, 74.2 mmol), paraformaldehyde (5.29 g) and potassium carbonate (2.28 g) were used to conduct the process similar to that shown in (1) of the Preparation 6, thus obtaining 1.54 g (yield: 77%) of 6-hydroxymethyl-5-methylthio-7-oxo-7H-thieno[3,2-b]thiopyran.

NMR(CDCl$_3$) δ: 2.66(3H, s), 3.76(1H, t, J=7.0 Hz), 4.94(2H, d, J=7.0 Hz), 7.25(1H, d, J=5.3 Hz), 7.85(lH, d, J=5.3 Hz)

(2) The obtained compound (2.16 g, 8.84 mmol) was suspended in dichloromethane (120 ml), added with 3,4-dihydro-2H-pyran (8 ml, 87.68 mmol) and p-toluenesulfonic acid monohydrate (32.8 mg, 0.172 mmol), successively, under ice-cooled stirring and stirred at room temperature for 4 hours. Then, the reaction mixture was added with dichloromethane (100 ml), washed with an aqueous solution of saturated sodium hydrogencarbonate (50 ml×2 times) and saturated saline solution, successively, and dried over anhydrous magnesium sulfate. The solvent was removed under reduced pressure and the residue was purified by column chromatography (Wako Gel™ C-200: dichloromethane-ethyl acetate=8:1), to obtain 2.26 g (yield: 78%) of 5-methylthio-7-oxo-6-(2-tetrahydropyranyl)oxymethyl-7H-thieno[3,2-b]thiopyran.

NMR(CDCl$_3$) δ: 1.51–1.84(6H, m), 2.66(3H, s), 3.58–3.64(1H, m), 3.98–4.09(1H, m), 4.74(1H, d, J=10.6

Hz), 4.87–4.89(1H, m), 5.05(1H, d, J=10.6 Hz), 7.21(1H, d, J=5.3 Hz), 7.76(1H, d, J=5.3 Hz)

(3) The obtained compound (1.26 g, 3.83 mmol) and metachloroperbenzoic acid (660 mg, 3.82 mmol) were used to conduct the process similar to that shown in (2) of the Preparation 2, thus obtaining 839 mg (yield: 64%) of 5-methylsulfinyl-7-oxo-6-(2-tetrahydropyranyl) oxymethyl-7H-thieno[3,2-b]thiopyran.

NMR(CDCl$_3$) δ: 1.56–1.84(6H, m), 3.07(3H, d, J=7.0 Hz), 3.56–3.66(1H, m), 3.87–3.98(1H, m), 4.46(1H, d, J=12.2 Hz), 4.74(1H, d, J=12.2 Hz), 4.81–4.84(1H, m), 4.99(1H, d, J=12.2 Hz), 5.31(1H, d, J=12.2 Hz), 7.39(1H, d, J=5.3 Hz), 7.89(1H, d, J=5.3 Hz)

(4) The obtained compound (482 mg, 1.4 mmol) was dissolved in tetrahydrofuran (15 ml) and added with 1N sodium hydrogensulfide (2.1 ml) under ice-water cooling, and stirred at room temperature for 30 minutes. The solvent was removed under reduced pressure to obtain the titled compound. This compound is used in the succeeding reaction without further purification.

Preparation 8: Preparation of sodium salt of 6-bromo-5-mercapto-7-oxo-7H-thieno[3,2-b]thiopyran (1) 5-Methylthio-7-oxo-7H-thieno[3,2-b]thiopyran (2.14 g, 10 mmol) was dissolved in acetic acid (140 ml) and added dropwise with bromine (0.96 ml). The reaction mixture was stirred at 50° C. for 16 hours. The resulting precipitates were collected by filtration, washed with water and dried. The reaction product was purified by column chromatography(Wako Gel™ C-200: dichloromethane-ethyl acetate=15:1) to obtain 1.98 g (yield: 67%) of 6-bromo-5-methylthio-7-oxo-7H-thieno[3,2-b]thiopyran.

NMR(CDCl$_3$) δ: 2.68(3H, s), 7.26(1H, d, J=5.3 Hz), 7.79(1H, d, J=5.3 Hz).

(2) The obtained compound (2.77 g, 9.4 mmol) and metachloroperbenzoic acid (1.96 g, 9.1 mmol) were used to conduct the procedure similar to that shown in (2) of the Preparation 2, thus obtaining 2.31 g (yield: 79%) of 6-bromo-5-methylsulfinyl-7-oxo-7H-thieno[3,2-b]thiopyran.

NMR(CDCl$_3$) δ: 3.07(1H, s), 7.44(1H, d, J=5.3 Hz), 7.92(1H, d, J=5.3 Hz)

(3) The obtained compound (430 mg, 1.4 mmol) and 1N sodium hydrogensulfide (2.1 ml) were used to conduct the procedure similar to that shown in (4) of the Preparation 7, thus obtaining the titled compound.

Preparation 9: Preparation of sodium salt of 5-mercapto-3-nitro-7-oxo-7H-thieno[3,2-b]thiopyran (1) Mixed acid of nitric acid (1.51 ml) with sulfric acid (5.15 ml) was cooled to −15° C. and added dropwise with a solution of 5-methylthio-7-oxo-7H-thieno[3,2-b]thiopyran (1.07 g, 5 mmol) in sulfric acid (4.9 ml). After further stirring at the temperature for one hour and at room temperature for 5 hours, the reaction mixture was injected into ice water (300 ml) and stirred for a while. Then, the resulting precipitates were collected by filtration, washed with water and dried. The reaction product was washed with diisopropylether to obtain 1.15 g (yield: 83%) of 5-methylsulfinyl-3-nitro-7-oxo-7H-thieno[3,2-b]thiopyran.

MS m/z: 275(M$^+$)

NMR(DMSO-d$_6$) δ: 3.06(3H, s), 7.48(1H, s), 9.54(1H, s)

(2) The obtained compound (276 mg, 1 mmol) and 1N sodium hydrogensulfide (1.5 ml) were used to conduct the procedure similar to that shown in (4) of the Preparation 7, thus obtaining the titled compound.

EXAMPLE 1

Preparation of 7β-amino-3-[2-(4-oxo-4H-1-benzothiopyran-2-yl)thiovinyl]-3-cephem-4-carboxylic acid benzhydryl ester (1) 7β-Tert-butoxycarbonylamino-3-(2-trifluoromethanesulfonyloxyvinyl)-3-cephem-4-carboxylic acid benzhydryl ester (trans isomer) (3.9 g, 6.1 mmol) was dissolved in anhydrous DMF (80 ml), added with 2-mercapto-4-oxo-4H-1-benzothiopyran (3.5 g, 18.3 mmol) and N-ethyldiisopropylamine (0.63 g, 4.87 mmol), successively, and stirred at room temperature under argon gas atmosphere for 24 hours. The reaction product was added with ethyl acetate (350 ml), washed with an aqueous solution of saturated sodium hydrogencarbonate (150 ml×2 times) and dried over anhydrous magnesium sulfate. The solvent was removed under reduced pressure and the residue was purified by column chromatography (Wago Gel™ C-200, methylene chloride-ethyl acetate (8:1)) to obtain 3.56 g (yield: 85.4%) of 7β-tert-butoxycarbonylamino-3-[2-(4-oxo-4H-1-benzothiopyran-2-yl)thiovinyl]-3-cephem-4-carboxylic acid benzhydryl ester as yellow-red froth.

NMR(CDCl$_3$) δ: 1.47(9H, s), 3.60(1H, d, J=17.8 Hz), 3.70(1H, d, J=17.8 Hz), 5.03(1H, d, J=5.0 Hz), 5.30(1H, d, J=9.6 Hz), 5.69(1H, dd, J=5.0 Hz, 9.6 Hz), 6.67(1H, d, J=15.5 Hz), 7.00(2H, s), 7.30–7.65(14H, m), 8.48(1H, d, J=7.9 Hz)

(2) The obtained compound (3.56 g, 5.2 mmol) was suspended in acetonitrile (100 ml), added with p-toluenesulfonic acid monohydrate (5 g, 26.0 mmol) and stirred at room temperature for 2.5 hours. The reaction mixture was added with ethyl acetate (200 ml) and an aqueous solution of saturated sodium hydrogencarbonate (100 ml) and stirred for a while. Then, ethyl acetate layer was collected, washed with saturated saline solution and dried over anhydrous magnesium sulfate. The solvent was removed under reduced pressure and the residue was crystallized from ether to obtain 1.5 g (yield: 49%) of the titled compound as yellow powder.

NMR(CDCl$_3$) δ: 3.60(1H, d, J=17.5 Hz), 3.69(1H, d, J=17.5 Hz), 4.82(1H, d, J=5.3 Hz), 5.01(1H, d, J=5.3 Hz), 6.62(1H, d, J=15.5 Hz), 6.97(1H, s), 7.02(1H, s), 7.22–7.70 (14H, m), 8.47(1H, d, J=7.9 Hz)

The following compounds were obtained from the corresponding starting materials and in the procedure similar to that shown in the Example 1.

7β-Amino-3-[2-(7-fluoro-4-oxo-4H-1-benzothiopyran-2-yl)thiovinyl]-3-cephem-4-carboxylic acid benzhydryl ester NMR(CDCl$_3$) δ: 3.63(2H, ABq, J=17.5 Hz), 4.82(1H, d, J=5.3 Hz), 5.00(1H, d, J=4.9 Hz), 6.59(1H, d, J=15.5 Hz), 6.94(1H, s), 7.01(1H, s), 7.19–7.49(13H, m), 8.48(1H, dd, J=5.9 Hz, 8.6 Hz)

7β-Amino-3-[2-(7-chloro-4-oxo-4H-1-benzothiopyran-2-yl)thiovinyl]-3-cephem-4-carboxylic acid benzhydryl ester NMR(CDCl$_3$) δ: 3.63(2H, ABq, J=17.8 Hz), 4.82(1H, brs), 5.01(1H, d, J=5.3 Hz), 6.68(1H, d, J=15.5 Hz), 6.94 (1H, s), 7.02(1H, s), 7.28–7.46(13H, m), 8.39(1H, d, J=8.5 Hz)

7β-Amino-3-[2-(7-methoxy-4-oxo-4H-1-benzothiopyran-2-yl)thiovinyl]-3-cephem-4-carboxylic acid benzhydryl ester NMR(CDCl$_3$) δ: 3.77(2H, ABq, J=17.5 Hz), 3.90(3H, s), 4.99(1H, d, J=4.9 Hz), 5.17(1H, d, J=4.9 Hz), 6.74(1H, d, J=15.5 Hz), 6.95(1H, s), 6.99(1H, s), 7.07–7.64(13H, m), 8.40(1H, d, J=8.9 Hz)

7β-Amino-3-[2-(4-oxo-5-trifluoromethyl-4H-1-benzothiopyran-2-yl)thiovinyl]-3-cephem-4-carboxylic acid benzhydryl ester NMR(CDCl$_3$) δ: 3.65(2H, ABq, J=17.5 Hz), 4.99(1H, d, J=4.9 Hz), 5.17(1H, d, J=4.9 Hz), 6.69(1H, d, J=15.5 Hz), 6.98(1H, s), 6.99(1H, s), 7.21–7.40(11H, m), 7.64–7.69(2H, m), 7.92(1H, d, J=7.9 Hz)

7β-Amino-3-[2-(4-oxo-7-trifluoromethyl-4H-1-benzothiopyran-2-yl)thiovinyl]-3-cephem-4-carboxylic acid benzhydryl ester NMR(CDCl$_3$) δ: 3.64(2H, ABq, J=17.5 Hz), 4.82(1H, d, J=4.9 Hz), 5.01(1H, d, J=4.9 Hz), 6.58(1H, d, J=15.5 Hz), 7.00(1H, s), 7.03(1H, s), 7.28–7.46(11H, m), 7.73–7.79(2H, m), 8.58(1H, d, J=8.2 Hz)

7β-Amino-3-[2-(6,7,8-trifluoro-4-oxo-4H-1-benzothiopyran-2-yl)thiovinyl]-3-cephem-4-carboxylic acid benzhydryl ester NMR(CDCl$_3$) δ: 3.64(2H, ABq, J=17.5 Hz), 4.82(1H, d, J=5.2 Hz), 5.02(1H, d, J=5.2 Hz), 6.56(1H, d, J=15.5 Hz), 6.93(1H, s), 7.02(1H, s), 7.26–7.45(11H, m), 8.07–8.15(1H, m)

7β-Amino-3-[2-(7-hydroxy-4-oxo-4H-1-benzothiopyran-2-yl)thiovinyl]-3-cephem-4-carboxylic acid benzhydryl ester NMR(DMSO-d$_6$) δ: 3.58(2H, ABq, J=17.5 Hz), 4.83(1H, d, J=4.9 Hz), 5.03(1H, d, J=4.9 Hz), 7.00(1H, s), 7.02(1H, s), 7.06(1H, d, J=15.5 Hz), 7.12–7.83(13H, m), 8.09(1H, d, J=8.6 Hz), 10.76(1H, brs)

7β-Amino-3-[2-(7-oxo-7H-thiopyrano[3,2-b]furan-5-yl)thiovinyl]-3-cephem-4-carboxylic acid benzhydryl ester NMR(CDCl$_3$) δ: 3.60(2H, ABq, J=17.8 Hz), 4.81(1H, d, J=5.0 Hz), 5.00(1H, d, J=5.0 Hz), 6.55(1H, d, J=15.2 Hz), 6.74(1H, d, J=2.0 Hz), 7.01(1H, s), 7.13(1H, s), 7.20–7.50 (11H, m), 7.82(1H, d, J=2.0 Hz)

7β-Amino-3-[2-(7-morpholino-4-oxo-4H-1-benzothiopyran-2-yl)thiovinyl]3-cephem-4-carboxylic acid benzhydryl ester NMR(CDCl$_3$) δ: 3.28(4H, t, J=4.9 Hz), 3.63(2H, q, J=17.5 Hz), 3.86(4H, t, J=4.9 Hz), 4.80(1H, d, J=5.3 Hz), 4.99(1H, d, J=5.3 Hz), 6.63(1H, d, J=15.5 Hz), 6.77(1H, d, J=2.6 Hz), 7.01(1H, s), 7.04(1H, dd, J=2.3 Hz, 8.9 Hz), 7.27(1H, d, J=15.5 Hz), 7.30–7.46(11H, m), 8.32(1H, d, J=8.9 Hz)

7β-Amino-3-[2-(4-oxo-7-piperidino-4H-1-benzothiopyran-2-yl)thiovinyl]-3-cephem-4-carboxylic acid benzhydryl ester NMR(CDCl$_3$) δ: 1.68(6H, brs), 3.38(4H, brs), 3.63(2H, q, J=17.5 Hz), 4.80(1H, d, J=5.3 Hz), 4.90(1H, d, J=5.3 Hz), 6.63(1H, d, J=15.5 Hz), 6.75(1H, d, J=2.3 Hz), 6.68(1H, s), 7.01(1H, s), 7.03(1H, dd, J=2.3 Hz, 8.9 Hz), 7.21(1H, d, J=15.5 Hz), 7.26–7.39(10H, m), 8.27(1H, d, J=8.9 Hz)

7β-Amino-3-[2-(7-oxo-7H-thieno[3,2-b]thiopyran-5-yl)thiovinyl]-3-cephem-4-carboxylic acid benzhydryl ester NMR(CDCl$_3$) δ: 3.58(1H, d, J=17.8 Hz), 3.67(1H, d, J=17.8 Hz), 4.81(1H, d, J=5.3 Hz), 5.00(1H, d, J=5.3 Hz), 6.58(1H, d, J=15.5 Hz), 7.00(1H, s), 7.01(1H, s), 7.24(1H, d, J=5.3 Hz), 7.27–7.46(11H, m), 7.83(1H, d, J=5.3 Hz)

7β-Amino-3-[2-(2-chloro-4-oxo-4H-thieno[2,3-b]thiopyran-6-yl)thiovinyl]-3-cephem-4-carboxylic acid benzhydryl ester NMR(CDCl$_3$) δ: 3.60(2H, ABq, J=17.8 Hz), 4.81(1H, d, J=5.0 Hz), 4.99(1H, d, J=5.0 Hz), 6.52(1H, d, J=15.2 Hz), 6.98(1H, s), 7.00(1H, s), 7.20–7.47(11H, m), 7.64(1H, s)

7β-Amino-3-[2-(4-oxo-7-(4-benzyloxycarbonylpiperazin-1-yl)-4H-1-benzothiopyran-2-yl)-thiovinyl]-3-cephem-4-carboxylic acid benzhydryl ester NMR(CDCl$_3$) δ: 3.38(4H, brs), 3.60–3.69(6H, m), 4.79 (1H, d, J=4.9 Hz), 4.98(1H, d, J=4.9 Hz), 5.17(2H, s), 6.61(1H, d, J=15.5 Hz), 6.76(1H, d, J=2.3 Hz), 6.87(1H, s), 7.01(1H, s), 7.02(1H, dd, J=2.3 Hz, 8.9 Hz), 7.13–7.46(16H, m), 8.31(1H, dd, J=8.9 Hz)

7β-Amino-3-[2-(8-oxo-8H-thiopyrano[2,3-b]pyrazin-6-yl)thiovinyl]-3-cephem-4-carboxylic acid benzhydryl ester NMR(CDCl$_3$) δ: 3.65(2H, ABq, J=17.8 Hz), 4.83(1H, d, J=5.3 Hz), 5.02(1H, d, J=5.3 Hz), 6.56(1H, d, J=15.2 Hz), 7.11(1H, s), 7.26(1H, s), 7.20–7.45(11H, m), 8.70(1H, d, J=2.0 Hz), 8.88(1H, d, J=2.0 Hz)

7β-Amino-3-[2-(6-bromo-7-oxo-7H-thieno[3,2-b]thiopyran-5-yl)thiovinyl]-3-cephem-4-carboxylic acid benzhydryl ester NMR(CDCl$_3$) δ: 3.63(1H, d, J=17.5 Hz), 3.72(1H, d, J=17.5 Hz), 4.85(1H, br), 5.03(1H, d, J=5.3 Hz), 6.56(1H, d, J=15.2 Hz), 7.06(1H, s), 7.23–7.43(12H, m), 7.79(1H, d, J=5.3 Hz)

7β-Amino-3-[2-(3-nitro-7-oxo-7H-thieno[3,2-b]thiopyran-5-yl)thiovinyl]-3-cephem-4-carboxylic acid benzhydryl ester NMR(CDCl$_3$) δ: 3.60(1H, d, J=17.8 Hz), 3.68(1H, d, J=17.8 Hz), 4.83(1H, d, J=5.0 Hz), 5.02(1H, d, J=5.0 Hz), 6.57(1H, d, J=15.5 Hz), 7.02(2H, s), 7.27–7.46(11H, m), 8.83(1H, s)

EXAMPLE 2

Preparation of 7β-amino-3-[2-(7-chloromethyl-4-oxo-4H-1-benzothiopyran-2-yl)thiovinyl]-3-cephem-4-carboxylic acid benzhydryl ester 7β-Tert-butoxycarbonylamino-3-[2-(7-hydroxymethyl-4-oxo-4H-1-benzothiopyran-2-yl)thiovinyl]-3-cephem-4-carboxylic acid benzhydryl ester (330 mg, 0.46 mmol) was suspended in anhydrous benzene (10 ml), added dropwise with thionyl chloride (0.55 ml, 7.59 mmol) while stirred at room temperature. Then, the reaction mixture was stirred at 50 minutes, added with ice water and extracted with ethyl acetate (50 ml). Ethyl acetate layer was washed with saturated saline solution and dried over magnesium sulfate. The solvent was removed under reduced pressure and the residue was crystallized from isopropyl ether to obtain 300 mg (yield: 89%) of 7β-tert-butoxycarbonylamino-3-[2(7-chloromethyl-4-oxo-4H-1-benzothiopyran-2-yl)thiovinyl]-3-cephem-4-carboxylic acid benzhydryl ester. Further, the process similar to that shown in (2) of the Example 1 was conducted to obtain 160 mg (yield: 62%) of the titled compound.

NMR(CDCl$_3$): 3.63(2H, ABq, 17.5 Hz), 4.64(2H, s), 4.81(1H, d, J=5.3 Hz), 5.01(1H, d, J=5.3 Hz), 6.60(1H, d, J=15.5 Hz), 6.96(1H, s), 7.02(1H, s), 7.20–7.60(13H, m), 8.44(1H, d, J=7.9 Hz)

EXAMPLE 3

Preparation of 7β-amino-3-[2-(6-chloromethyl-7-oxo-7H-thieno[3,2-b]thiopyran-5-yl)thiovinyl]-3-cephem-4-carboxylic acid benzhydryl ester (1) 7β-Tert-butoxycarbonylamino-3-[2-[7-oxo-6-(2-tetrahydropyranyl)oxymethyl]-7H-thieno[3,2-b]thiopyran-5-yl]thiovinyl]-3-cephem-4-carboxylic acid benzhydryl ester (400 mg, 0.5 mmol) was added with an aqueous solution of 50% acetic acid (80 ml) and stirred at 40° C. for 7 hours under heating. The reaction mixture was added with dichloromethane (50 ml), washed with water (50 ml×2 times) and dried over anhydrous magnesium sulfate. The solvent was removed under reduced pressure and the residue was crystallized by diisopropyl ether to obtain 273 mg (yield: 76%) of 7β-tert-butoxycarbonylamino-3-[2-(6-hydroxymethyl-7-oxo-7H-thieno[3,2-b]thiopyran-5-yl)thiovinyl]-3-cephem-4-carboxylic acid benzhydryl ester.

NMR(CDCl$_3$) δ: 1.47(9H, s), 3.57(1H, d, J=17.8 Hz), 3.66(1H, d, J=17.8 Hz), 4.88(2H, s), 5.01(1H, d, J=5.0 Hz), 5.25(1H, d, J=9.0 Hz), 5.64–5.70(1H, m), 6.64(1H, d, J=15.5 Hz), 6.98(1H, s), 7.23(1H, d, J=5.3 Hz), 7.29–7.45(11H, m), 7.84(1H, d, J=5.3 Hz)

(2) The obtained compound (273 mg, 0.38 mmol) and thionyl chloride (0.46 ml, 6.25 mmol) were used to conduct the procedure similar to that shown in the Example 2, thus obtaining 206.3 mg (yield: 73%) of 7β-tert-butoxycarbonylamino-3-[2-(6-chloromethyl-7-oxo-7H-thieno[3,2-b]thiopyran-5-yl)thiovinyl]-3-cephem-4-carboxylic acid benzhydryl ester. Further, the process similar to that shown in (2) of the Example 1 was conducted to obtain 132 mg (yield: 74%) of the titled compound.

NMR(CDCl$_3$) δ: 3.58(1H, d, J=17.5 Hz), 3.67(1H, d, J=17.5 Hz), 4.83(1H, d, J=5.0 Hz), 4.88(2H, s), 5.00(1H, d, J=5.0 Hz), 6.59(1H, d, J=15.2 Hz), 7.05(1H, s), 7.20(1H, d, J=5.3 Hz), 7.28–7.47(11H, m), 7.82(1H, d, J=5.3 Hz)

EXAMPLE 4

Preparation of 7-[2-(2-thienyl)acetamide]-3-[2-(4-oxo-4H-1-benzothiopyran-2-yl)thiovinyl]3-cephem-4-carboxylic acid (compound 1)

(1) 7β-Amino-3-[2-(4-oxo-4H-1-benzothiopyran-2-yl)thiovinyl]-3-cephem-4-carboxylic acid benzhydryl ester (160 mg, 0.27 mmol) was dissolved in anhydrous dichloromethane (5 ml), added with thiophene-2-acetic acid (57.6 mg, 0.40 mmol) and dicyclohexylcarbodiimide (82.5 mg, 0.40 mmol) at room temperature, successively, and stirred at the temperature for 24 hours. The reaction mixture was added with ethyl acetate (20 ml) and the insoluble matter was filtered. The filtrate was washed with an aqueous solution of saturated sodium hydrogencarbonate (20 ml×2 times) and saturated saline solution, successively, and dried over anhydrous magnesium sulfate. The solvent was removed under reduced pressure and the residue was purified by column chromatography (Lobar Column™ Si60, Size A (Merck), dichloromethane-ethyl acetate (8:1)) and evaporated to dryness. The resulting crystals were washed with ether to obtain 80 mg (yield: 42%) of 7-[2-(2-thienyl)acetamide]-3-[2-(4-oxo-4H-1-benzothiopyran-2-yl)thiovinyl]-3-cephem-4-carboxylic acid benzhydryl ester as light yellow crystals.

NMR(CDCl$_3$) δ: 3.55(1H, d, J=17.5 Hz), 3.63(1H, d, J=17.5 Hz), 3.87(2H, s),5.03(1H, d, J=5.0 Hz), 5.87(1H, dd, J=5.0 Hz, 9.0 Hz), 6.32(1H, d, J=9.0 Hz), 6.65(1H, d, J=15.5 Hz), 6.97(1H, s), 6.99–7.03(3H, m), 7.25–7.65(15H, m), 8.48(1H, d, J=7.9 Hz)

(2) The obtained compound (70 mg, 0.099 mmol) was dissolved in dichloromethane (3 ml), added with anisole (0.22 ml, 1.98 mmol) and cooled to 0–5° C. The cooled product was added with trifluoroacetic acid (0.17 ml, 1.98 mmol), stirred at room temperature for 4 hours and re-cooled to 0–5° C. The re-cooled product was added with isopropyl ether (30 ml) under stirring and the resultant precipitates were collected by filtration and fully washed with isopropyl ether to obtain 48 mg (yield: 89%) of the titled compound as yellow powder.

FAB-MS m/z: 543 [M+H]$^+$

NMR(DMSO-d$_6$) δ: 3.69(1H, d, J=17.5 Hz), 4.05(1H, d, J=17.5 Hz), 5.18(1H, d, J=5.0 Hz), 5.73(1H, dd, J=5.0 Hz, 8.2 Hz), 6.94(2H, m), 7.08(1H, s), 7.14(1H, d, J=15.0 Hz), 7.26(1H, d, J=15.0 Hz), 7.35(1H, dd, J=2.0 Hz, 4.6 Hz), 7.61(1H, dt, J=1.0 Hz, 8.0 Hz), 7.69(1H, dt, J=1.0 Hz, 8.0 Hz), 7.82(1H, dd, J=1.0 Hz, 8.0 Hz), 8.25(1H, dd, J=1.0 Hz, 8.0 Hz), 9.20(1H, d, J=8.2 Hz), 13.80(1H, br)

EXAMPLE 5

Preparation of 7-[2-(2-thienyl)acetamide]-3-[2-(7-fluoro-4-oxo-4H-1-benzothiopyran-2-yl)thiovinyl]-3-cephem-4-carboxylic acid (compound 2)

In the same manner as that in (1) of the Example 4, 7β-amino-3-[2-(7-fluoro-4-oxo-4H-1-benzothiopyran-2-yl)thiovinyl]-3-cephem-4-carboxylic acid benzhydryl ester (120 mg, 0.20 mmol), thiophene-2-acetic acid (45 mg, 0.32 mmol) and dicyclohexylcarbodiimide (66 mg, 0.32 mmol) were used to obtain 100 mg (yield: 69%) of 7-[2-(2-thienyl)acetamide]-3-[2-(7-fluoro-4-oxo-4H-1-benzothiopyran-2-yl)thiovinyl]-3-cephem-4-carboxylic acid benzhydryl ester. The obtained compound (93 mg, 0.13 mmol), anisole (0.28 ml, 2.56 mmol) and trifluoroacetic acid (0.20 ml, 2.56 mmol) were used to conduct the procedure similar to that shown in (2) of the Example 4 to obtain 24 mg (yield: 33%) of the titled compound.

FAB-MS m/z: 561 [M+H]$^+$

NMR(DMSO-d$_6$) δ: 3.86(2H, s), 3.95(2H, ABq, J=17.5 Hz), 5.27(1H, d, J=4.9 Hz), 5.81(1H, dd, J=4.9 Hz, 8.2 Hz), 7.02–7.06(2H, m), 7.17(1H, s), 7.22(1H, d, J=15.5 Hz), 7.33(1H, d, J=15.5 Hz), 7.46(1H, dd, J=1.3 Hz, 4.9 Hz), 7.55–7.62(1H, m), 7.98(1H, dd, J=2.3 Hz, 9.4 Hz), 8.44(1H, dd, J=6.0 Hz, 8.9 Hz), 9.28(1H, dd, J=8.2 Hz)

EXAMPLE 6

Preparation of 7-[2-(2-thienyl)acetamide]-3-[2-(7-chloro-4-oxo-4H-1-benzothiopyran-2-yl)thiovinyl]-3-cephem-4-carboxylic acid (compound 3)

In the same manner as that shown in (1) of the Example 4, 7β-amino-3-[2-(7-chloro-4-oxo-4H-1-benzothiopyran-2-yl)thiovinyl]-3-cephem-4-carboxylic acid benzhydryl ester (105 mg, 0.20 mmol), thiophene-2-acetic acid (110 mg, 0.27 mmol) and dicyclohexylcarbodiimide (55 mg, 0.27 mmol) were used to obtain 86 mg (yield: 68%) of 7-[2-(2-thienyl)acetamide]-3-[2-(7-chloro-4-oxo-4H-1-benzothiopyran-2- yl)thiovinyl]-3-cephem-4-carboxylic acid benzhydryl ester. The obtained compound (80 mg, 0.11 mmol), anisole (0.23 ml, 2.10 mmol) and trifluoroacetic acid (0.21 ml, 2.70 mmol) were used to conduct the procedure similar to that shown in (2) of the Example 4, thus obtaining 14mg (yield: 22%) of the titled compound.

FAB-MS m/z: 577 [M+H]$^+$

NMR(DMSO-$d_6$) δ: 3.77(2H, ABq, J=17.9 Hz), 3.85(2H, s), 5.18(1H, d, J=4.9 Hz), 5.71(1H, dd, J=4.9 Hz, 8.2 Hz), 6.94–7.03(2H, m), 7.07(1H, d, J=15.2 Hz), 7.09(1H, s), 7.26(1H, d, J=15.2 Hz), 7.37(1H, dd, J=1.3 Hz, 4.9 Hz), 7.66(1H, dd, J=2.3 Hz, 8.6 Hz), 8.13(1H, d, J=2.3 Hz), 8.28(1H, d, J=8.6 Hz), 9.18(1H, d, J=8.2 Hz)

EXAMPLE 7

Preparation of 7-[2-(2-thienyl)acetamide]-3-[2-(7-methoxy-4-oxo-4H-1-benzothiopyran-2-yl) thiovinyl]-3-cephem-4-carboxylic acid (compound 4)

In the same manner as that shown in (1) of the Example 4, 7β-amino-3-[2-(7-methoxy-4-oxo-4H-1-benzothiopyran-2-yl)thiovinyl]-3-cephem-4-carboxylic acid benzhydryl ester (117 mg, 0.19 mmol), thiophene-2-acetic acid (41 mg, 0.28 mmol) and dicyclohexylcarbodiimide (59 mg, 0.28 mmol) were used to obtain 107 mg (yield: 76%) of 7-[2-(2-thienyl)acetamide]-3-[2-(7-methoxy-4-oxo-4H-1-benzothiopyran-2-yl)thiovinyl]-3-cephem-4-carboxylic acid benzhydryl ester. The obtained compound (90 mg, 0.15 mmol), anisole (0.32 ml, 2.94 mmol) and trifluoroacetic acid (0.23 ml, 2.98 mmol) were used to conduct the procedure similar to that shown in (2) of the Example 4 to obtain 51 mg (yield: 61%) of the titled compound.

FAB-MS m/z: 573 [M+H]$^+$

NMR(DMSO-$d_6$) δ: 3.77(2H, ABq, J=17.9 Hz), 3.86(2H, s), 3.88(3H, s), 5.17(1H, d, J=4.9 Hz), 5.71(1H, dd, J=4.9 Hz, 8.2 Hz), 6.93–6.96(2H, m), 6.99(1H, s), 7.08(1H, d, J=15.5 Hz), 7.17(1H, d, J=2.6 Hz, 9.2 Hz), 7.22(1H, d, J=15.5 Hz), 7.36(1H, dd, J=1.6 Hz, 4.9 Hz), 7.40(1H, d, J=2.6 Hz), 8.22(1H, d, J=9.2 Hz), 9.16(1 H, d, J=7.9 Hz)

EXAMPLE 8

Preparation of 7-[2-(2-thienyl)acetamide]-3-[2-(4-oxo-5-trifluoromethyl-4H-1-benzothiopyran-2-yl) thiovinyl]-3-cephem-4-carboxylic acid (compound 5)

In the same manner as that shown in (1) of the Example 4, 7β-amino-3-[2-(4-oxo-5-trifluoromethyl-4H-1-benzothiopyran-2-yl)thiovinyl]-3-cephem-4-carboxylic acid benzhydryl ester (210 mg, 0.32 mmol), thiophene-2-acetic acid (92 mg, 0.64 mmol) and dicyclohexylcarbodiimide (132 mg, 0.64 mmol) were used to obtain 226 mg (yield: 91%) of 7-[2-(2-thienyl)acetamide]-3-[2-(4-oxo-5-trifluoromethyl-4H-1-benzothiopyran-2-yl)thiovinyl]-3-cephem-4-carboxylic acid benzhydryl ester. The obtained compound (240 mg, 0.31 mmol), anisole (0.67 ml, 6.10 mmol) and trifluoroacetic acid (0.47 ml, 6.10 mmol) were used to conduct the procedure similar to that shown in (2) of the Example 4, thus obtaining 89 mg (yield: 47%) of the titled compound.

FAB-MS m/z: 611 [M+H]$^+$

NMR(DMSO-$d_6$) δ: 3.71(2H, s), 3.80(2H, ABq, J=17.8 Hz), 5.12(1H, d, J=4.9 Hz), 5.67(1H, dd, J=4.9 Hz, 8.2 Hz), 6.87–6.91(2H, m), 7.04(1H, s), 7.05(1H, d, J=15.5 Hz), 7.19(1H, d, J=15.5 Hz), 7.31(1H, dd, J=1.6 Hz, 4.6 Hz), 7.87(1H, t, J=2.0 Hz), 7.97(1H, d, J=7.6 Hz), 8.10(1H, d, J=7.6 Hz), 9.12(1H, d, J=8.2 Hz)

EXAMPLE 9

Preparation of 7-[2-(2-thienyl)acetamide]-3-[2-(4-oxo-7-trifluoromethyl-4H-1-benzothiopyran-2-yl) thiovinyl]-3-cephem-4-carboxylic acid (compound 6)

In the same manner as that shown in (1) of the Example 4, 7β-amino-3-[2-(4-oxo-7-trifluoromethyl-4H-1-benzothiopyran-2-yl)thiovinyl]-3-cephem-4-carboxylic acid benzhydryl ester (102 mg, 0.15 mmol), thiophene-2-acetic acid (44 mg, 0.31 mmol) and dicyclohexylcarbodiimide (64 mg, 0.31 mmol) were used to obtain 98 mg (yield: 80%) of 7-[2-(2-thienyl)acetamide]-3-[2-(4-oxo-7-trifluoromethyl-4H-1-benzothiopyran-2-yl)thiovinyl]-3-cephem-4-carboxylic acid benzhydryl ester. The obtained compound (90 mg, 0.11 mmol), anisole (0.25 ml, 2.32 mmol) and trifluoroacetic acid (0.18 ml, 2.32 mmol) were used to conduct the procedure similar to that shown in (2) of the Example 4, thus obtaining 54 mg (yield: 76%) of the titled compound.

FAB-MS m/z: 611 [M+H]$^+$

NMR(DMSO-$d_6$) δ: 3.86(2H, s), 3.96(2H, ABq, J=17.8 Hz), 5.28(1H, d, J=4.9 Hz), 5.82(1H, dd, J=4.9 Hz, 8.2 Hz), 7.02–7.07(2H, m), 7.21(1H, d, J=15.2 Hz), 7.25(1H, s), 7.36(1H, d, J=15.5 Hz), 7.45(1H, dd, J=1.6 Hz, 4.9 Hz), 8.02(1H, dd, J=2.6 Hz, 8.6 Hz), 8.52(1H, d, J=2.6 Hz), 8.54(1H, d, J=8.6 Hz), 9.27(1H, d, J=7.9 Hz)

EXAMPLE 10

Preparation of 7-[2-(2-thienyl)acetamide]-3-[2-(6,7,8-trifluoro-4-oxo-4H-1-benzothiopyran-2-yl) thiovinyl]-3-cephem-4-carboxylic acid (compound 7)

In the same manner as that shown in (1) the Example 4, 7β-amino-3-[2-(6,7,8-trifluoro-4-oxo-4H-1-benzothiopyran-2-yl)thiovinyl]-3-cephem-4-carboxylic acid benzhydryl ester (155 mg, 0.24 mmol), thiophene-2-acetic acid (69 mg, 0.48 mmol) and dicyclohexylcarbodiimide (100 mg, 0.48 mmol) were used to obtain 163 mg (yield: 89%) of 7-[2-(2-thienyl)acetamide]-3-[2-(6,7, 8-trifluoro-4-oxo-4H-1-benzothiopyran-2-yl)thiovinyl]-3-cephem-4-carboxylic acid benzhydryl ester. The obtained compound (152 mg , 0.20 mmol), anisole (0.43 ml, 3.99 mmol) and trifluoroacetic acid (0.31 ml, 3.99 mmol) were used to conduct the procedure similar to that shown in (2) of the Example 4, thus obtaining 91 mg (yield: 77%) of the titled compound.

FAB-MS m/z: 597 [M+H]$^+$

NMR(DMSO-$d_6$) δ: 3.72(2H, s), 3.93(2H, ABq, J=17.5 Hz), 5.20(1H, d, J=4.9 Hz), 5.75(1H, dd, J=4.9 Hz, 8.2 Hz), 6.92–6.99(2H, m), 7.14(1H, d, J=15.5 Hz), 7.28(1H, d, J=15.5 Hz), 7.38(1H, dd, J=1.3 Hz, 6.5 Hz), 8.10–8.17(1H, m), 9.19(1H, d, J=8.2 Hz)

EXAMPLE 11

Preparation of 7-[2-(2-thienyl)acetamide]-3-[2-(7-hydroxy-4-oxo-4H-1-benzothiopyran-2-yl) thiovinyl]-3-cephem-4-carboxylic acid (compound 8)

In the same manner as that shown in (1) of the Example 4, 7β-amino-3-[2-(7-hydroxy-4-oxo-4H-1-benzothiopyran- 2-yl)thiovinyl]-3-cephem-4-carboxylic acid benzhydryl ester (329 mg, 0.54 mmol), thiophene-2-acetic acid (155 mg, 1.09 mmol) and dicyclohexylcarbodiimide (225 mg, 1.09 mmol) were used to obtain 339 mg (yield: 85%) of 7-[2-(2-thienyl)acetamide]-3-[2-(7-hydroxy-4-oxo-4H-1-benzothiopyran-2-yl)thiovinyl]-3-cephem-4-carboxylic acid benzhydryl ester. The obtained compound (315 mg, 0.43 mmol), anisole (0.94 ml, 8.69 nmmol) and trifluoroacetic acid (0.67 ml, 8.69 mmol) were used to conduct the procedure similar to that shown in (2) of the Example 4, thus obtaining 86 mg (yield: 35%) of the titled compound.

FAB-MS m/z: 559 [M+H]+

NMR(DMSO-$d_6$) δ: 3.86(2H, s), 3.99(2H, ABq, J=17.2 Hz), 5.27(1H, d, J=4.9 Hz), 5.81(1H, dd, J=4.9 Hz, 8.3 Hz), 7.03(1H, s), 7.03–7.05(2H, m), 7.07(1H, dd, J=15.2 Hz), 7.10–7.13(1H, m), 7.33(1H, d, J=15.2 Hz), 7.45–7.58(2H, m), 8.44(1H, d, J=8.9 Hz), 9.27(1H, d, J=8.3 Hz), 10.90(1H, brs)

EXAMPLE 12

Preparation of 7-[2-(2-thienyl)acetamide]-3-[2-(7-oxo-7H-thiopyrano[3,2-b]furan-5-yl)thiovinyl]-3-cephem-4-carboxylic acid (compound 9)

In the same manner as that shown in (1) of the Example 4, 7β-amino-3-[2-(7-oxo-7H-thiopyrano[3,2-b]furan-5-yl)thiovinyl]-3-cephem-4-carboxylic acid benzhydryl ester (60 mg, 0.104 mmol), thiophene-2-acetic acid (22.3 mg, 0.156 mmol) and dicyclohexylcarbodiimide (32.3 mg, 0.156 mmol) were used to obtain 40 mg (yield: 55%) of 7-[2-(2-thienyl)acetamide]-3-[2-(7-oxo-7H-thiopyrano[3,2-b]furan-5-yl)thiovinyl]-3-cephem-4-carboxylic acid benzhydryl ester as light yellow powder. The obtained compound (39 mg, 0.056 mmol), anisole (0.12 ml, 1.12 mmol) and trifluoroacetic acid (0.086 ml, 1.12 mmol) were used to conduct the procedure similar to that shown in (2) of the Example 4, thus obtaining 23 mg (yield: 77%) of the titled compound as yellow powder.

FAB-MS m/z: 533 [M+H]+

NMR(DMSO-$d_6$) δ: 3.65(1H, d, J=17.8 Hz), 3.77(2H, s), 3.98(1H, d, J=17.8 Hz), 5.16(1H, d, J=5.0 Hz), 5.70(1H, dd, J=5.0 Hz, 8.0 Hz), 6.94(2H, m), 7.07(1H, d, J=15.5 Hz), 7.08(1H, d, J=15.5 Hz), 7.19(2H, s+d, J=1.6 Hz), 7.34(1H, dd, J=1.6 Hz, 4.6 Hz), 8.27(1H, d, J=1.6 Hz), 9.16(1H, d, J=8.0 Hz)

EXAMPLE 13

Preparation of 7-[2-(2-thienyl)acetamide]-3-[2-(7-morpholino-4-oxo-4H-1-benzothiopyran-2-yl)thiovinyl]-3-cephem-4-carboxylic acid (compound 10)

In the same manner as that shown in (1) of the Example 4, 7β-amino-3-[2-(7-morpholino4-oxo-4H-1-benzothiopyran-2-yl)thiovinyl]-3-cephem-4-carboxylic acid benzhydryl ester (90 mg, 0.13 mmol), thiophene-2-acetic acid (38 mg, 0.27 mmol) and dicyclohexylcarbodiimide (56 mg, 0.27 mmol) were used to obtain 66 mg (yield: 62%) of 7-[2-(2-thienyl)acetamide]-3-[2-(7-morpholino-4-oxo-4H-1-benzothiopyran-2-yl)thiovinyl]-3-cephem-4-carboxylic acid benzhydryl ester. The obtained compound (60 mg, 0.08 mmol), anisole (0.17 ml, 1.52 mmol) and trifluoroacetic acid (0.12 ml, 1.52 mmol) were used to conduct the procedure similar to that shown in (2) of the Example 4, thus obtaining 25 mg (yield: 52%) of the titled compound.

FAB-MS m/z: 628 [M+H]+

NMR(DMSO-$d_6$) δ: 3.42(4H, br), 3.82(4H, br), 3.86(2H, s), 3.97(2H, q, J=17.8 Hz), 5.27(1H, d, J=4.9 Hz), 5.81(1H, dd, J=4.9 Hz, 8.3 Hz), 7.01(1H, s), 7.03–7.05(2H, m), 7.18(1H, d, J=15.5 Hz), 7.27–7.33(3H, m), 7.46(1H, d, J=4.6 Hz), 8.19(1H, d, J=8.9 Hz), 9.27(1H, d, J=8.3 Hz)

EXAMPLE 14

Preparation of 7-[2-hydroxyimino-2-(2-aminothiazol-4-yl)acetamide]-3-[2-(4-oxo-4H-1-benzothiopyran-2-yl)thiovinyl]-3-cephem-4-carboxylic acid In the same manner as that shown in (1) of the Example 4, 7β-amino-3-[2-(4-oxo-4H-1-benzothiopyran-2-yl)thiovinyl]-3-cephem-4-carboxylic acid benzhydryl ester (1.5 g, 2.57 mmol), (Z)-2-trityloxyimino-2-(2-tritylaminothiazol-4-yl)acetate (2.6 g, 3.86 mmol) and dicyclohexylcarbodiimide (0.8 g, 3.86 mmol) were used to obtain 2.0 g (yield: 63%) of 7-[2-trityloxyimino-2-(2-tritylaminothiazol-4-yl)acetamide]-3-[2-(4-oxo-4H-1-benzothiopyran-2-yl)thiovinyl]-3-cephem-4-carboxylic acid benzhydryl ester as orange powder. The obtained compound (1.8 g, 1.45 mmol) was dissolved in a mixed solution of acetic acid (64 ml) and water (6 ml) and stirred under heating at 40–45° C. for 3.5 hours. The solvent was removed under reduced pressure and at the temperature below 35° C. and the residue was crystallized by ether to obtain 1.0 g of 7-[2-hydroxyimino-2-(2-aminothiazol-4-yl)acetamide]-3-[2-(4-oxo-4H-1-benzothiopyran-2-yl)thiovinyl]-3-cephem-4-carboxylic acid benzhydryl ester. Then, the obtained ester was added to a mixed liquid of anisole (4.2 ml, 38.6 mmol) with trifluoroacetic acid (21.2 ml, 275.2 mmol) cooled in the ice-water bath and stirred at that temperature for 30 minutes and further at room temperature for 1.5 hours. Then, the reaction mixture was cooled again in the ice-water bath, added with diisopropyl ether (160 ml) and stirred for 30 minutes. The resulting precipitates were collected by filtration and fully washed with diisopropyl ether to obtain 834 mg (yield: 97%) of the titled compound.

FAB-MS m/z: 588 [M+H]+

NMR(DMSO-$d_6$) δ: 3.70(1H, d, J=18.0 Hz), 4.02(1H, d, J=18.0 Hz), 5.25(1H, d, J=4.6 Hz), 5.84(1H, dd, J=4.6 Hz, 8.0 Hz), 6.77(1H, s), 7.08(1H, s), 7.13(1H, d, J=15.0 Hz), 7.26(1H, d, J=15.0 Hz), 7.62(1H, t, J=7.0 Hz), 7.74(1H, t, J=7.0 Hz), 7.85(1H, d, J=7.0 Hz), 8.30(1H, d, J=7.0 Hz), 9.62(1H, d, J=8.0 Hz)

EXAMPLE 15

Preparation of 7-[2-(1H-tetrazol-1-yl)acetamide]-3-[2-(4-oxo-4H-1-benzothiopyran-2-yl)thiovinyl]-3-cephem-4-carboxylic acid (compound 12)

In the same manner as that shown in (1) of the Example 4, 7β-amino-3-[2-(4-oxo-4H-1-benzothiopyran-2-yl)thioylnyl]-3-cephem-4-carboxylic acid benzhydryl ester (160 mg, 0.27 mmol), 1-tetrazolacetic acid (38.4 mg, 0.3 mmol) and dicyclohexylcarbodiimide (61.9 mg, 0.3 mmol) were used to obtain 30 mg (yield: 16%) of 7-[2-(1H-tetrazol-1-yl)acetamide]-3-[2-(4-oxo-4H-1-benzothiopyran-2-yl)thiovinyl]-3-cephem-4-carboxylic acid benzhydryl ester as orange powder. The obtained compound (30.3 mg, 0.044 mmol), anisole (0.095 ml, 0.88 mmol) and trifluoroacetic acid (0.07 ml, 0.88 mmol) were used to conduct the procedure similar to that shown in (2) of the Example 4, thus obtaining 14.6 mg (yield: 63%) of the titled compound.

FAB-MS m/z: 529 [M+H]+

NMR(DMSO-d$_6$) δ: 3.67(1H, d, J=17.8 Hz), 4.03(1H, d, J=17.8 Hz), 5.15(1H, d, J=5.0 Hz), 5.33(2H, s), 5.74(1H, dd, J=5.0 Hz, 8.0 Hz), 7.03(1H, s), 7.10(1H, d, J=15.4 Hz), 7.20(1H, d, J=15.4 Hz), 7.57(1H, t, J=7.0 Hz), 7.69(1H, t, J=7.0 Hz), 7.81(1H, d, J=7.0 Hz), 8.25(1H, d, J=8.0 Hz), 9.31(1H, s), 9.52(1H, d, J=8.0 Hz)

EXAMPLE 16

Preparation of 7-[2-(4-thiazolyl)acetamide]-3-[2-(4-oxo-4H-1-benzothiopyran-2-yl)thiovinyl]-3-cephem-4-carboxylic acid (compound 13)

In the same manner as that shown in (1) of the Example 4, 7β-amino-3-[2-(4-oxo-4H-1-benzothiopyran-2-yl)thiovinyl]-3-cephem-4-carboxylic acid benzhydryl ester (160 mg, 0.27 mmol), 2-(4-thiazolyl)acetic acid (60 mg, 0.41 mmol) and dicyclohexylcarbodiimide (85 mg, 0.41 mmol) were used to obtain 123 mg (yield: 64%) of 7-[2-(4-thiazolyl)acetamide]-3-[2-(4-oxo-4H-1-benzothiopyran-2-yl)thiovinyl]3-cephem-4-carboxylic acid benzhydryl ester as orange powder. The obtained compound (118.4 mg, 0.17 mmol), anisole (0.37 ml, 3.4 mmol) and trifluoroacetic acid (1.31 ml, 17.0 mmol) were used to conduct the procedure similar to that shown in (2) of the Example 4, thus obtaining 75 mg (yield: 81%) of the titled compound.

FAB-MS m/z: 544 [M+H]$^+$

NMR(DMSO-d$_6$) δ: 3.79(1H, d, J=17.8 Hz), 4.12(1H, d, J=17.8 Hz), 3.87(2H, s), 5.27(1H, d, J=5.0 Hz), 5.85(1H, dd, J=5.0 Hz, 8.0 Hz), 7.18(1H, s), 7.23(1H, d, J=15.5 Hz), 7.34(1H, d, J=15.5 Hz), 7.56(1H, d, J=2.0 Hz), 7.72(1H, t, J=8.0 Hz), 7.84(1H, t, J=8.0 Hz), 7.96(1H, d, J=7.3 Hz), 8.40(1H, d,6 J=8.0 Hz), 9.13(1H, d, J=2.0 Hz), 9.23(1H, d, J=8.0 Hz)

EXAMPLE 17

Preparation of 7-[2-(2-aminothiazol-4-yl)acetamide]-3-[2-(4-oxo-4H-1-benzothiopyran-2-yl)thiovinyl]-3-cephem-4-carboxylic acid (compound 14)

In the same manner as that shown in (1) of the Example 4, 7β-amino-3-[2-(4-oxo-4H-1-benzothiopyran-2-yl)thiovinyl]-3-cephem-4-carboxylic acid benzhydryl ester (160 mg, 0.27 mmol), 2-(2-tritylaminothiazol-4-yl)acetic acid (168 mg, 0.41 mmol) and dicyclohexylcarbodiimide (85 mg, 0.41 mmol) were used to obtain 180 mg (yield: 69%) of 7-[2-(2-tritylaminothiazol-4-yl)acetamide]-3-[2-(4-oxo-4H-1-benzothiopyran-2-yl)thiovinyl]-3-cephem-4-carboxylic acid benzhydryl ester as orange powder. The obtained compound (173 mg, 0.18 mmol), anisole (0.39 ml, 3.6 mmol) and trifluoroacetic acid (1.39 ml, 18 mmol) were used to conduct the procedure similar to that shown in (2) of the Example 4, thus obtaining 75 mg (yield: 75%) of the titled compound.

FAB-MS m/z: 559 [M+H]$^+$

NMR(DMSO-d$_6$) δ: 3.66(1H, d, J=18.0 Hz), 4.00(1H, d, J=18.0 Hz), 3.68(2H, s), 5.14(1H, d, J=5.0 Hz), 5.72(1H, dd, J=5.0 Hz, 8.0 Hz), 6.53(1H, s), 7.02(1H, s), 7.08(1H, d, J=15.5 Hz), 7.19(1H, d, J=15.5 Hz), 7.57(1H, t, J=8.0 Hz), 7.69(1H, t, J=8.0 Hz), 7.80(1H, d, J=8.0 Hz), 8.25(1H, d, J=8.0 Hz), 9.11(1H, d, J=8.0 Hz),

EXAMPLE 18

Preparation of 7-[2-cyclopentyloxyimino-2-(2-aminothiazol-4-yl)acetamide]-3-[2-(4-oxo-4H-1-benzothiopyran-2-yl)thiovinyl]-3-cephem-4-carboxylic acid (compound 15)

In the same manner as that shown in (1) of the Example 4, 7β-amino-3-[2-(4-oxo-4H-1-benzothiopyran-2-yl)thiovinyl]-3-cephem-4-carboxylic acid benzhydryl ester (150 mg, 0.26 mmol), (Z)-2-cyclopentyloxyimino-2-(2-tritylaminothiazol-4-yl)acetic acid (194 mg, 0.39 mmol) and dicyclohexylcarbodiimide (80.5 mg, 0.39 mmol) were used to obtain 180 mg (yield: 65%) of 7-[2-cyclopentyloxyimino-2-(2-tritylaminothiazol-4-yl)acetamide]-3-[2-(4-oxo-4H-1-benzothiopyran-2-yl)thiovinyl]-3-cephem-4-carboxylic acid benzhydryl ester as orange powder. The obtained compound (150 mg, 0.14 mmol), anisole (0.32 ml, 3.0 mmol) and trifluoroacetic acid (1.6 ml, 21 mmol) were used to conduct the procedure similar to that shown in (2) of the Example 4, thus obtaining 90 mg (yield: 98%) of the titled compound as yellow powder.

FAB-MS m/z: 656 [M+H]$^+$

NMR(DMSO-d$_6$) δ: 1.51–2.00(8H, m), 3.70(1H, d, J=18.0 Hz), 4.05(1H, d, J=18.0 Hz), 4.71(1H, m), 5.25(1H, d, J=4.9 Hz), 5.84(1H, dd, J=4.9 Hz, 7.9 Hz), 6.78(1H, s), 7.08(1H, s), 7.15(1H, d, J=15.5 Hz), 7.25(1H, d, J=15.5 Hz), 7.62(1H, t, J=8.0 Hz), 7.74(1H, t, J=8.0 Hz), 7.84(1H, d, J=8.0 Hz), 8.30(1H, d, J=8.9 Hz), 9.63(1H, d, J=7.9 Hz)

EXAMPLE 19

Preparation of 7-[2-fluoromethyloxyimino-2-(2-aminothiazol-4-yl)acetamide]-3-[2-(4-oxo-4H-1-benzothiopyran-2-yl)thiovinyl]-3-cephem-4-carboxylic acid (compound 16)

In the same manner as that shown in (1) of the Example 4, 7β-amino-3-[2-(4-oxo-4H-1-benzothiopyran-2-yl)thiovinyl]-3-cephem-4-carboxylic acid benzhydryl ester (150 mg, 0.26 mmol), (Z)-2-fluoromethyloxyimino-2-(2-tritylaminothiazol-4-yl)acetic acid (180 mg, 0.39 mmol) and dicyclohexylcarbodiimide (80.5 mg, 0.39 mmol) were used to obtain 174 mg (yield: 65%) of 7-[2-fluoromethyloxyimino-2-(2-tritylaminothiazol-4-yl)acetamide]-3-[2-(4-oxo-4H-1benzothiopyran-2-yl)thiovinyl]-3-cephem-4-carboxylic acid benzhydryl ester as orange powder. The obtained compound (150 mg, 0.15 mmol), anisole (0.32 ml, 3.0 mmol) and trifluoroacetic acid (1.6 g, 21 mmol) were used to conduct the procedure similar to that shown in (2) of the Example 4, thus obtaining 80 mg (yield: 86%) of the titled compound as light brown powder.

FAB-MS m/z: 620 [M+H]$^+$

NMR(DMSO-d$_6$) δ: 3.71(1H, d, J=18.0 Hz), 4.03(1H, d, J=18.0 Hz), 5.26(1H, d, J=5.0 Hz), 5.75 and 5.84(2H, d+dd, J=55 Hz, J=5.0 Hz, 8.0 Hz), 6.93(1H, s), 7.07(1H, s), 7.13(1H, d, J=15.0 Hz), 7.26(1H, d, J=15.0 Hz), 7.63(1H, td, J=1.5 Hz, 8.0 Hz), 7.74(1H, td, J=1.5 Hz, 8.0 Hz), 7.84(1H, d, J=8.0 Hz), 8.31(1H, dd, J=1.5 Hz, 8.0 Hz), 9.87(1H, d, J=8.0 Hz)

EXAMPLE 20

Preparation of 7-[2-hydroxyimino-2-(2-aminothiazol-4-yl)acetamide]-3-[2-(7-oxo-7H-thiopyrano[3,2-b]furan-5-yl)thiovinyl]-3-cephem-4-carboxylic acid (compound 17)

In the same manner as that shown in (1) of the Example 4, 7β-amino-3-[2-(7-oxo-7H-thiopyrano[3,2-b]furan-5-yl)thiovinyl]-3-cephem-4-carboxylic acid benzhydryl ester (150 mg, 0.26 mmol), (Z)-2-trityloxyimino-2-(2-tritylaminothiazol-4-yl)acetic acid (263 mg, 0.39 mmol) and dicyclohexylcarbodiimide (81 mg, 0.39 mmol) were used to obtain 100 mg (yield: 31.3%) of 7-[2-trityloxyimino-2-(2-tritylaminothiazol-4-yl)acetamide]-3-[2-(7-oxo-7H-thiopyrano[3,2-b]furan-5-yl)thiovinyl]-3-cephem-4- carboxylic acid benzhydryl ester as orange powder. The obtained compound (60 mg, 0.049 mmol), anisole (0.1 ml, 0.98 mmol) and trifluoroacetic acid (0.53 ml, 6.86 mmol) were used to conduct the procedure similar to that shown in (2) of the Example 4, thus obtaining 18 mg (yield: 64%) of the titled compound as yellow-brown powder.

FAB-MS m/z: 578 [M+H]$^+$

NMR(DMSO-$d_6$) δ: 3.65(1H, d, J=17.5 Hz), 3.96(1H, d, J=17.5 Hz), 5.24(1H, d, J=5.0 Hz), 5.84(1H, dd, J=5.0 Hz, 8.0 Hz), 6.70(1H, s), 7.10(1H, d, J=15.2 Hz), 7.14–7.40(6H, m), 8.28(1H, brs), 9.55(1H, d, J=8.0 Hz), 11.50(1H, brs)

EXAMPLE 21

Preparation of 7-[2-hydroxyimino-2-(2-aminothiazol-4-yl)acetamide]-3-[2-(7-fluoro-4-oxo-4H-1-benzothiopyran-2-yl)thiovinyl]-3-cephem-4-carboxylic acid (compound 18)

In the same manner as that shown in (1) of the Example 4, 7β-amino-3-[2-(7-fluoro-4-oxo-4H-1-benzothiopyran-2-yl)thiovinyl]-3-cephem-4-carboxylic acid benzhydryl ester (216 mg, 0.36 mmol), (Z)-2-trityloxyimino-2-(2-tritylaminothiazol-4-yl)acetic acid (481 mg, 0.72 mmol) and dicyclohexylcarbodiimide (148 mg, 0.72 mmol) were used to obtain 108 mg (yield: 24%) of 7-[2-trityloxyimino-2-(2-tritylaminothiazol-4-yl)acetamide]-3-[2-(7-fluoro-4-oxo-4H-1-benzothiopyran-2-yl)thiovinyl]-3-cephem-4-carboxylic acid benzhydryl ester. The obtained compound (105 mg, 0.083 mmol), anisole (0.18 ml, 1.67 mmol) and trifluoroacetic acid (0.90 ml, 11.62 mmol) were used to conduct the procedure similar to that shown in (2) of the Example 4, thus obtaining 37 mg (yield: 74%) of the titled compound as yellow-brown powder.

FAB-MS m/z: 533 [M+H]$^+$

NMR(DMSO-$d_6$) δ: 3.77(1H, d, J=17.5 Hz), 4.10(1H, d, J=17.5 Hz), 5.33(1H, d, J=4.9 Hz), 5.93(1H, dd, J=4.9 Hz, 7.9 Hz), 6.83(1H, s), 7.17(1H, s), 7.34(1H, d, J=15.2 Hz), 7.40(1H, brs), 7.58(1H, dt, J=2.3 Hz, 8.6 Hz), 7.98(1H, dd, J=2.6 Hz, 9.2 Hz), 8.46(1H, dd, J=5.9 Hz, 8.1 Hz), 9.69(1H, d, J=7.9 Hz), 11.77(1H, brs)

EXAMPLE 22

Preparation of 7-[2-(2-thienyl)acetamide]-3-[2-(4-oxo-7-piperidino-4H-1-benzothiopyran-2-yl) thiovinyl]-3-cephem-4-carboxylic acid (compound 19)

In the same manner as that shown in (1) of the Example 4, 7β-amino-3-[2-(4-oxo-7-piperidino-4H-1-benzothiopyran-2-yl)thiovinyl]-3-cephem-4-carboxylic acid benzhydryl ester (115 mg, 0.17 mmol), thiophene-2-acetic acid (49 mg, 0.34 mmol) and dicyclohexylcarbodiimide (71 mg, 0.34 mmol) were used to obtain 90 mg (yield: 66%) of 7-[2-(2-thienyl)acetamide]-3-[2-(4-oxo-7-piperidino-4H-1-benzothiopyran-2-yl)thiovinyl]-3-cephem-4-carboxylic acid benzhydryl ester. The obtained compound (80 mg, 0.10 mmol), anisole (0.22 ml, 2.02 mmol) and trifluoroacetic acid (0.15 ml, 2.02 mmol) were used to conduct the procedure similar to that shown in (2) of the Example 4, thus obtaining 51 mg (yield: 80%) of the titled compound.

FAB-MS m/z: 626 [M+H]$^+$

NMR(DMSO-$d_6$) δ: 1.68(6H, brs), 3.50(4H, brs), 3.85 (2H, s), 3.94(2H, ABq, J=17.5 Hz), 5.26(1H, d, J=4.9 Hz), 5.81(1H, dd, J=4.9 Hz, 8.2 Hz), 6.97(1H, s), 7.02–7.06(2H, m), 7.18(1H, d, J=15.2 Hz), 7.21(1H, d, J=2.3 Hz), 7.26(1H, dd, J=2.3 Hz, 8.9 Hz), 7.29(1H, d, J=15.2 Hz), 7.46(1H, dd, J=1.3 Hz, 5.0 Hz), 8.14(1H, d, J=8.9 Hz), 9.27(1H, d, J=8.2 Hz)

EXAMPLE 23

Preparation of 7-[2-(2-thienyl)acetamide]-3-[2-(7-oxo-7H-thieno[3,2-b]thiopyran-5-yl)thiovinyl]-3-cephem-4-carboxylic acid (compound 20)

In the same manner as that shown in (1) of the Example 4, 7β-amino-3-[2-(7-oxo-7H-thieno[3,2-b]thiopyran-5-yl) thiovinyl]-3-cephem-4-carboxylic acid benzhydryl ester (122 mg, 0.21 mmol), thiophene-2-acetic acid (33 mg, 0.23 mmol) and dicyclohexylcarbodiimide (48 mg, 0.23 mmol) were used to obtain 51 mg (yield: 34%) of 7-[2-(2-thienyl) acetamide]-3-[2-(7-oxo-7H-thieno[3,2-b]thiopyran-5-yl) thiovinyl]-3-cephem-4-carboxylic acid benzhydryl ester. The obtained compound (49 mg, 0.07 mmol), anisole (0.15 ml, 1.38 mmol) and trifluoroacetic acid (0.30 ml, 4.14 mmol) were used to conduct the procedure similar to that shown in (2) of the Example 4, thus obtaining 19.4 mg (yield: 51%) of the titled compound.

FAB-MS m/z: 549 [M+H]$^+$

NMR(DMSO-$d_6$) δ: 3.68(1H, d, J=17.8 Hz), 3.77(2H, s), 4.02(1H, d, J=17.8 Hz), 5.17(1H, d, J=5.0 Hz), 5.73(1H, dd, J=4.6 Hz, 8.3 Hz), 6.94–6.97(2H, m), 7.10(1H, d, J=15.5 Hz), 7.11(1H, s), 7.23(1H, d, J=15.1 Hz), 7.37(1H, dd, J=1.6 Hz, 5.0 Hz), 7.64(1H, d, J=5.3 Hz), 8.27(1H, d, J=5.3 Hz), 9.19(1H, d, J=8.3 Hz)

EXAMPLE 24

Preparation of 7-[2-(2-thienyl)acetamide]-3-[2-(2-chloro-4-oxo-4H-thieno[2,3-b]thiopyran-6-yl) thiovinyl]-3-cephem-4-carboxylic acid (compound 21)

In the same manner as that shown in (1) of the Example 4, 7β-amino-3-[2-(2-chloro-4-oxo-4H-thieno[2,3-b] thiopyran-6-yl)thiovinyl]-3-cephem-4-carboxylic acid benzhydryl ester (60 mg, 0.10 mmol), thiophene-2-acetic acid (20.5 mg, 0.14 mmol) and dicyclohexylcarbodiimide (29.7 mg, 0.14 mmol) were used to obtain 30 mg (yield: 42%) of 7-[2-(2-thienyl)acetamide]-3-[2-(2-chloro-4-oxo-4H-thieno [2,3-b]thiopyran-6-yl)thiovinyl]-3-cephem-4-carboxylic acid benzhydryl ester. The obtained compound (24 mg, 0.03 mmol), anisole (0.07 ml, 0.64 mmol) and trifluoroacetic acid (0.05 ml, 0.64 mmol) were used to conduct the procedure similar to that shown in (2) of the Example 4, thus obtaining 13 mg (yield: 70%) of the titled compound.

FAB-MS m/z: 583 [M+H]$^+$

NMR(DMSO-$d_6$) δ: 3.65(1H, d, J=17.8 Hz), 3.77(2H, s), 3.99(1H, d, J=17.8 Hz), 5.17(1H, d, J=4.6 Hz), 5.72(1H, dd, J=4.6 Hz, 8.0 Hz), 6.94(2H, m), 7.08(1H, d, J=15.2 Hz), 7.10(1H, s), 7.22(1H, d, J=15.2 Hz), 7.35(1H, dd, J=1.7 Hz, 4.6 Hz), 7.57(1H, s), 9.17(1H, d, J=8.0 Hz)

EXAMPLE 25

Preparation of 7-[2-(2-thienyl)acetamide]-3-[2-(4-oxo-7-(piperazin-1-yl)-4H-1-benzothiopyran-2-yl) thiovinyl]-3-cephem-4-carboxylic acid.hydrochloride (compound 22)

In the same manner as that shown in (1) of the Example 4, 7β-amino-3-[2-(4-oxo-7-(4-benzyloxycarbonylpiperazin-1-yl)-4H-1-benzothiopyran-2-yl)thiovinyl]-3-cephem-4- carboxylic acid benzhydryl ester (113 mg, 0.14 mmol), thiophene-2-acetic acid (40 mg, 0.28 mmol) and dicyclohexylcarbodiimide (58 mg, 0.28 mmol) were used to obtain 82 mg (yield: 62%) of 7-[2-(2-thienyl)acetamide]-3-[2-(4-oxo-7-(4-benzyloxycarbonylpiperazin-1-yl)-4H-1-benzothiopyran-2-yl)thiovinyl]-3-cephem-4-carboxylic acid benzhydryl ester. The obtained compound (80 mg, 0.086 mmol) was dissolved in anisole (5 ml, 46 mmol), added with anhydrous aluminium chloride (69 mg, 0.517 mmol) under ice bathing and stirred for 12 hours. The reaction liquid was injected into ice water (15 ml) and acidified by 2N hydrochloric acid into pH 1.5. The reaction product was washed with ethyl acetate and the water layer was freeze-dried. The residue was purified by reversed phase column chromatography (Wako Gel™ LP-40C18, Wako Junyaku K.K.) with water-acetonitrile (1:1) to obtain 18 mg (yield: 32%) of the titled compound as light yellow powder.

FAB-MS m/z: 627 [M+H—HCl]$^+$

NMR(DMSO-d$_6$) δ: 3.22(4H, brs), 3.24–3.74(6H, m), 3.78(2H, s), 5.11(1H, d, J=5.0 Hz), 5.61(1H, dd, J=5.0 Hz, 8.5 Hz), 6.95(1H, s), 6.97–7.15(2H, m), 7.17–7.26(3H, m), 7.37(1H, d, J=15.2 Hz), 7.38(1H, dd, J=1.3 Hz, 4.9 Hz), 8.09(1H, d, J=8.9 Hz), 9.15(1H, d, J=8.5 Hz)

EXAMPLE 26

Preparation of 7-[2-hydroxyimino-2-(2-aminothiazol-4-yl)acetamide]-3-[2-(7-oxo-7H-thieno[3,2-b]thiopyran-5-yl)thiovinyl]-3-cephem-4-carboxylic acid (compound 23)

In the same manner as that shown in (1) of the Example 4, 7β-amino-3-[2-(7-oxo-7H-thieno[3,2-b]thiopyran-5-yl)thiovinyl]-3-cephem-4-carboxylic acid benzhydryl ester (183 mg, 0.31 mmol), (Z)-2-trityloxyimino-2-(2-tritylaminothiazol-4-yl)acetic acid (333 mg, 0.5 mmol) and dicyclohexylcarbodiimide (102 mg, 0.5 mmol) were used to obtain 250 mg (yield: 65%) of 7-[2-trityloxyimino-2-(2-tritylaminothiazol-4-yl)acetamide]-3-[2-(7-oxo-7H-thieno[3,2-b]thiopyran-5-yl)thiovinyl]-3-cephem-4-carboxylic acid benzhydryl ester as yellow powder. The obtained compound (201 mg, 0.16 mmol), anisole (0.35 ml, 3.2 mmol) and trifluoroacetic acid (0.74 ml, 9.6 mmol) were used to conduct the procedure similar to that shown in (2) of the Example 4, thus obtaining 73.7 mg (yield: 65%) of the titled compound.

FAB-MS m/z: 707 [M+H]$^+$

NMR(DMSO-d$_6$) δ: 3.68(1H, d, J=17.8 Hz), 3.99(1H, d, J=17.5 Hz), 5.24(1H, d, J=5.0 Hz), 5.85(1H, dd, J=5.0 Hz, 8.0 Hz), 6.75(1H, s), 7.12(1H, d, J=15.2 Hz), 7.23(1H, d, J=15.2 Hz), 7.64(1H, d, J=5.3 Hz), 8.27(1H, d, J=5.3 Hz), 9.61(1H, d, J=8.0 Hz), 11.7(1H,s)

EXAMPLE 27

Preparation of 7-[2-(2-thienyl)acetamide]-3-[2-(8-oxo-8H-thiopyrano[2,3-b]pyrazin-6-yl)thiovinyl]-3-cephem-4-carboxylic acid (compound 24)

In the same manner as that shown in (1) of the Example 4, 7β-amino-3-[2-(8-oxo-8H-thiopyrano[2,3-b]pyrazin-6-yl)thiovinyl]-3-cephem-4-carboxylic acid benzhydryl ester (105 mg, 0.18 mmol), thiopheneacetic acid(38.2 mg, 0.27 mmol) and dicyclohexylcarbodiimide (55.7 mg, 0.27 mmol) were used to obtain 80 mg (yield: 63%) of 7-[2-(2-thienyl)acetamide]-3-[2-(8-oxo-8H-thiopyrano[2,3-b]pyrazin-6-yl)thiovinyl]-3-cephem-4-carboxylic acid benzhydryl ester. The obtained compound (65 mg, 0.09 mmol), anisole (0.2 ml, 1.9 mmol) and trifluoroacetic acid (0.15 ml, 1.9 mmol) were used to conduct the procedure similar to that shown in (2) of the Example 4, thus obtaining 40 mg (yield: 50%) of the titled compound.

FAB-MS m/z: 545 [M+H]$^+$

NMR(DMSO-d$_6$): 3.71(1H, d, J=17.8 Hz), 3.78(2H, s), 4.08(1H, d, J=17.8 Hz), 5.19(1H, d, J=5 Hz), 5.74(1H, dd, J=5 Hz, 8.3 Hz), 6.94(2H, m), 7.10(1H, d, J=15.5 Hz), 7.21(1H, d, J=15.5 Hz), 7.31(2H, m), 8.88(1H, d, J=2 Hz), 8.95(1H, d, J=2 Hz), 9.20(1H, d, J=8.3 Hz)

EXAMPLE 28

Preparation of 7-[2-(2-thienyl)acetamide]-3-[2-(6-bromo-7-oxo-7H-thieno[3,2-b]thiopyran-5-yl)thiovinyl]-3-cephem-4-carboxylic acid (compound 25)

In the same manner as that shown in (1) of the Example 4, 7β-amino-3-[2-(6-bromo-7-oxo-7H-thieno[3,2-b]thiopyran-5-yl)thiovinyl]-3-cephem-4-carboxylic acid benzhydryl ester (135.5 mg, 0.2 mmol), thiopheneacetic acid (57.5 mg, 0.4 mmol) and dicyclohexylcarbodiimide (62.6 mg, 0.3 mmol) were used to obtain 71.7 mg (yield: 45%) of 7-[2-(2-thienyl)acetamide]-3-[2-(6-bromo-7-oxo-7H-thieno[3,2-b]thiopyran-5-yl)thiovinyl]-3-cephem-4-carboxylic acid benzhydryl ester. The obtained compound (45 mg, 0.057 mmol), anisole (0.12 ml, 1.14 mmol) and trifluoroacetic acid (0.09 ml, 1.14 mmol) were used to conduct the procedure similar to that shown in (2) of the Example 4, thus obtaining 35.5 mg (yield: 99%) of the titled compound.

FAB-MS m/z: 627 [M+H]$^+$

NMR(DMSO-d$_6$) δ: 3.74(1H, d, J=17.8 Hz), 3.78(2H, s), 4.04(1H, d, J=17.8 Hz), 5.22(1H, d, J=5.0 Hz), 5.77(1H, dd, J=5.0 Hz, 8.0 Hz), 6.93–6.98(2H, m), 7.07(1H, d, J=15.2 Hz), 7.36–7.38(1H, m), 7.39(1H, d, J=15.2 Hz), 7.68(1H, d, J=5.3 Hz), 8.26(1H, d, J=5.3 Hz), 9.20(1H, d, J=8.0 Hz)

EXAMPLE 29

Preparation of 7-[2-(2-thienyl)acetamide]-3-[2-(3-nitro-7-oxo-7H-thieno[3,2-b]thiopyran-5-yl)thiovinyl]-3-cephem-4-carboxylic acid (compound 26)

In the same manner as that shown in (1) of the Example 4, 7β-amino-3-[2-(3-nitro-7-oxo-7H-thieno[3,2-b]thiopyran-5-yl)thiovinyl]-3-cephem-4-carboxylic acid benzhydryl ester (125 mg, 0.197 mmol), thiopheneacetic acid (42 mg, 0.295 mmol) and dicyclohexylcarbodiimide (61 mg, 0.295 mmol) were used to obtain 108.8 mg (yield: 73%) of 7-[2-(2-thienyl)acetamide]-3-[2-(3-nitro-7-oxo-7H-thieno[3,2-b]thiopyran-5-yl)thiovinyl]-3-cephem-4-carboxylic acid benzhydryl ester. The obtained compound (108.8 mg, 0.143 mmol), anisole (0.3 ml, 2.86 mmol) and trifluoroacetic acid (0.7 ml, 8.59 mmol) were used to conduct the procedure similar to that shown in (2) of the Example 4, thus obtaining 50.5 mg (yield: 59%) of the titled compound.

FAB-MS m/z: 594 [M+H]$^+$

NMR(DMSO-d$_6$) δ: 3.68(1H, d, J=17.8 Hz), 3.77(2H, s), 4.04(1H, d, J=17.8 Hz), 5.19(1H, d, J=5.0 Hz), 5.73(1H, dd, J=5.0 Hz, 8.0 Hz), 6.94–6.96(2H, m), 7.11(1H, d, J=15.5 Hz), 7.22(1H, s), 7.27(1H, d, J=15.5 Hz), 7.34–7.36(1H, m), 9.19(1H, d, J=8.0 Hz), 9.49(1H, s)

EXAMPLE 30

Preparation of 7-(2-phenylacetamide)-3-[2-(4-oxo-4H-1-benzothiopyran-2-yl)thiovinyl]-3-cephem-4-carboxylic acid (compound 27)

In the same manner as that shown in (1) of the Example 4, 7β-amino-3-[2-(4-oxo-4H-1-benzothiopyran-2-yl)thiovinyl]-3-cephem-4-carboxylic acid benzhydryl ester (38 mg, 0.065 mmol), phenylacetic acid (15 mg, 0.11 mmol) and dicyclohexylcarbodiimide (23 mg, 0.11 mmol) were used to obtain 42 mg of 7-(2-phenylacetamide)-3-[2-(4-oxo-4H-1-benzothiopyran-2-yl)thiovinyl]-3-cephem-4-carboxylic acid benzhydryl ester. The obtained compound (40 mg, 0.057 mmol), anisole (0.1 ml, 0.92 mmol) and trifluoroacetic acid (0.1 ml, 1.29 mmol) were used to conduct the procedure similar to that shown in (2) of the Example 4, thus obtaining 15 mg (yield: 50%) of the compound.

FAB-MS m/z: 537 [M+H]$^+$

NMR(DMSO-$d_6$): 3.63(2H, d, J=8.9 Hz), 3.96(2H, ABq, J=17.8 Hz), 5.25(1H, d, J=4.9 Hz), 5.80(1H, dd, J=4.9 Hz, 8.2 Hz), 7.17–7.42(8H, m), 7.69–7.75(1H, m), 7.96(1H, d, J=7.9 Hz), 8.40(1H, d, J=7.9 Hz), 9.25(1H, d, J=8.2 Hz)

EXAMPLE 31

Preparation of 7-[2-(2-thienyl)acetamide]-3-[2-(7-isothiuronium methyl-4-oxo-4H-1-benzothiopyran-2-yl)thiovinyl]-3-cephem-4-carboxylic acid.formate (compound 28)

(1) In the same manner as that shown in (1) of the Example 4, 7β-amino-3-[2-(7-chloromethyl-4-oxo-4H-1-benzothiopyran-2-yl)thiovinyl]-3-cephem-4-carboxylic acid benzhydryl ester (150 mg, 0.24 mmol), thiopheneacetic acid (50.5 mg, 0.36 mmol) and dicyclohexylcarbodiimide (74.3 mg, 0.36 mmol) were used to obtain 60mg (yield: 33%) of 7-[2-(2-thienyl)acetamide]-3-[2-(7-chloromethyl-4-oxo-4H-1-benzothiopyran-2-yl)thiovinyl]-3-cephem-4-carboxylic acid benzhydryl ester. The obtained compound (50 mg, 0.066 mmol) was dissolved in a mixed solvent of ethanol (2.5 ml) with dimethylformamide (1 ml), added with thiourea (75.4 mg, 0.99 mmol) and stirred at room temperature for 3 days. The solvent was removed under reduced pressure and the reaction mixture was dissolved in methanol (4 ml). The insoluble matter was filtered out and the filtrate was dealt with Cephadex LH-20 (charged to have 3 cm in dia. and 7 cm in length: methanol) to collect firstly flowing yellow fraction. The solvent was removed under reduced pressure and the residue was crystallized with isopropyl ether to obtain 44 mg (yield: 80%) of 7-[2-(2-thienyl)acetamide]-3-[2-(7-isothiuronium methyl-4-oxo-4H-1-benzothiopyran-2-yl)thiovinyl]-3-cephem-4-carboxylic acid benzhydryl ester.hydrochloride.

FAB-MS m/z: 797[M+H—HCl]$^+$

NMR(DMSO-$d_6$) δ: 3.71(1H, d, J=18.0 Hz), 3.78(2H, s), 4.10(1H, d, J=18.0 Hz), 4.62(2H, s), 5.24(1H, d, J=5.0 Hz), 5.80(1H, dd, J=5.0 Hz, 9.0 Hz), 6.90–7.50(17H, m), 7.65 (1H, d, J=8.2 Hz), 7.86(1H, s), 8.30(1H, d, J=8.2 Hz)

(2) The obtained compound (40 mg, 0.048 mmol) was added to formic acid (0.8 ml), stirred at 40–42° C. for one hour under heating. The solvent was removed under reduced pressure and the resulting product was crystallized with ether to obtain 30 mg (yield: 99%) of the titled compound.

FAB-MS m/z: 631[M+H—HCOOH]$^+$

NMR(DMSO-$d_6$+$D_2O$) δ: 3.68(1H, d, J=17.0 Hz), 3.77 (1H, s), 4.04(1H, d, J=17.0 Hz), 4.63(2H, s), 5.18(1H, d, J=5.0 Hz), 5.65(1H, m), 6.80–7.50(6H, m), 7.65(1H, d, J=8.5 Hz), 7.88(1H, s), 8.30(1H, d, J=8.5 Hz)

EXAMPLE 32

Preparation of 7-[2-(2-thienyl)acetamide]-3-[2-(6-isothiuronium methyl-7-oxo-7H-thieno[3,2-b]thiopyran-5-yl)thiovinyl]-3-cephem-4-carboxylic acid.trifluoro acetate (compound 29)

In the same manner as that shown in (1) of the Example 4, 7β-amino-3-[2-(6-chloromethyl-7-oxo-7H-thieno[3,2-b]thiopyran-5-yl)thiovinyl]-3-cephem-4-carboxylic acid benzhydryl ester (132.2 mg, 0.21 mmol), thiopheneacetic acid (44.1 mg, 0.31 mmol) and dicyclohexylcarbodiimide (64 mg, 0.31 mmol) were used to obtain 34 mg (yield: 21%) of 7-[2-(2-thienyl)acetamide]-3-[2-(6-chloromethyl-7-oxo-7H-thieno[3,2-b]thiopyran-5-yl)thiovinyl]-3-cephem-4-carboxylic acid benzhydryl ester. The obtained compound (34 mg, 0.045 mmol) and thiourea (51 mg, 0.668 mmol) were used to conduct the procedure similar to that shown in (1) of the Example 31, thus obtaining 25.1 mg (yield: 67%) of 7-[2-(2-thienyl)acetamide]-3-[2-(6-isothiuronium methyl-7-oxo-7H-thieno[3,2-b]thiopyran-5-yl)thiovinyl]-3-cephem-4-carboxylic acid benzhydryl ester.hydrochloride.

NMR(MeOD) δ: 3.71(1H, d, J=17.5 Hz), 3.82(2H, s), 3.90(1H, d, J=17.5 Hz), 5.18(1H, d, J=5.0 Hz), 5.79(1H, d, J=5.0 Hz), 6.94–6.96 (3H, m), 7.22–7.41(13H, m), 7.45(1H, d, J=5.3 Hz), 7.98(2H, s), 8.18(1H, d, J=5.3 Hz)

Further, the obtained compound (24.5 mg, 0.029 mmol) anisole (0.06 ml, 0.582 mmol) and trifluoroacetic acid (0.1 ml, 1.299 mmol) were used to conduct the procedure similar to that shown in (2) of the Example 4, thus obtaining 12.4 mg (yield: 67%) of the titled compound.

FAB-MS m/z: 637 [M+H—CF$_3$COOH]$^+$

NMR(DMSO-$d_6$) δ: 3.65(1H, d, J=17.5 Hz), 3.78(2H, s), 3.89(1H, d, J=17.5 Hz), 4.56(2H, s), 5.16(1H, d, J=5.0 Hz), 5.69(1H, dd, J=5.0 Hz, 8.0 Hz), 6.94–6.96(2H, m), 7.36–7.44(3H, m), 7.68(1H, d, J=5.3 Hz), 8.32(1H, d, J=5.3 Hz), 9.16(1H, d, J=8.0 Hz)

EXAMPLE 33

Preparation of 7-[2-(2-thienyl)acetamide]-3-[2-(4-oxo-4H-thiopyrano[2,3-b]pyridin-2-yl)thiovinyl]-3-cephem-4-carboxylic acid (compound 30)

In the same manner as that shown in (1) of the Example 1, 7-[2-(2-thienyl)acetamide]-3-(2-trifluoromethanesulfonyloxyvinyl-3-cephem-4-carboxylic acid benzhydryl ester (80 mg, 0.12 mmol), 2-mercapto-4-oxo-4H-thiopyrano[2,3-b]pyridine (58.7 mg, 0.3 mmol) and N-ethyldiisopropylamine (12.4 mg, 0.096 mmol) were used to obtain 7-[2-(2-thienyl)acetamide]-3-[2-(4-oxo-4H-thiopyrano[2,3-b]pyridin-2-yl)thiovinyl]-3-cephem-4-carboxylic acid benzhydryl ester. The obtained compound (35 mg, 0.49 mmol), anisole (0.1 ml 0.99 mmol) and trifluoroacetic acid (0.08 ml 0.99 mmol) were used to conduct the procedure similar to that shown in (2) of the Example 4, thus obtaining 16 mg (yield: 60%) of the titled compound.

FAB-MS m/z: 544 [M+H]$^+$

NMR(DMSO-$d_6$) δ: 3.71(1H, d, J=17.8 Hz), 3.77(2H, s), 4.08(1H, d, J=17.8 Hz), 5.19(1H, d, J=5.0 Hz), 5.74(1H, dd, J=5.0 Hz, 8.2 Hz), 6.95(2H, m), 7.12(1H, d, J=15.0 Hz), 7.13(1H, s), 7.28(1H, d, J=15.0 Hz), 7.35(1H, dd, J=2.0 Hz, 4.6 Hz), 7.67(1H, dd, J=4.6 Hz, 8.0 Hz), 8.60(1H, dd, J=1.7 Hz, 8.0 Hz), 8.85(1H, dd, J=1.7 Hz, 4.6 Hz), 9.20(1H, d, J=8.2 Hz)

EXAMPLE 34

Preparation of 7-[2-(2-thienyl)acetamide]-3-[2-(5-aminomethyl-2-chloro-4-oxo-4H-thieno[2,3-b]thiopyran-6-yl)thiovinyl]-3-cephem-4-carboxylic acid.trifluoroacetate (compound 31)

In the same manner as that shown in (1) of the Example 1, 7-[2-(2-thienyl)acetamide]-3-(2-trifluoromethanesulfonyloxyvinyl)-3-cephem-4-carboxylic acid benzhydryl ester (480 mg, 0.7 mmol), 5-tert-butoxycarbonylaminomethyl-2-chloro-4-oxo-6-mercapto-4H-thieno[2,3-b]thiopyran (232 mg, 0.7 mmol) and N-ethyldiisopropylamine (72.4 mg, 0.56 mmol) were used to obtain 174 mg (yield: 28.3%) of 7-[2-(2-thienyl)acetamide]-3-[2-(5-tert-butoxycarbonylaminomethyl-2-chloro-4-oxo-4H-thieno[2,3-b]thiopyran-6-yl)thiovinyl]-3-cephem-4-carboxylic acid benzhydryl ester. The obtained compound (40 mg, 0.046 mmol), anisole (0.1 ml, 0.92 mmol) and trifluoroacetic acid (0.071 ml, 0.92 mmol) were used to conduct the procedure similar to that shown in (2) of the Example 4, thus obtaining 14 mg (yield: 42%) of the titled compound.

FAB-MS m/z: 612 [M+H—CF$_3$COOH]$^+$

NMR(DMSO-d$_6$) δ: 3.60(1H, d, J=17.5 Hz), 3.77(2H, s), 3.86(1H, d, J=17.5 Hz), 4.11(2H, s), 5.13(1H, d, J=5.0 Hz), 5.68(1H, dd, J=5.0 Hz, 8.0 Hz), 6.85(1H, d, J=15.5 Hz), 6.95(2H, m), 7.27(1H, d, J=15.5 Hz), 7.33(11, dd, J=1.5, 4.5 Hz), 7.62(1H, s), 9.14(1H, d)

EXAMPLE 35

Preparation of sodium 7-[2-hydroxyimino-2-(2-aminothiazol-4-yl)acetamide]-3-[2-(4-oxo-4H-1-benzothiopyran-2-yl)thiovinyl]-3-cephem-4-carbonate (compound 11)

7-[2-hydroxyimino-2-(2-aminothiazol-4-yl)acetamide]-3-[2-(4-oxo-4H-1-benzothiopyran-2-yl)thiovinyl]-3-cephem-4-carboxylic acid (500 mg, 0.85 mmol) was suspended in water (30 ml) and adjusted by saturated sodium hydrogencarbonate into pH 7.6. The resulting solution was separated and purified by reversed phased column chromatography (RP-18, acetonitrile-water (3:7)). The obtained fraction was freeze-dried to obtain 260 mg (yield: 50%) of the titled compound.

Melting Point: >300° C. (decomp.)

FAB-MS m/z: 610 [M+Na]$^+$

NMR(DMSO-d$_6$) δ: 3.47(1H, d, J=16.5 Hz), 3.61(1H, d, J=16.5 Hz), 5.05(1H, d, J=5.0 Hz), 5.60(1H, dd, J=5.0 Hz, 9.0 Hz), 6.38(1H, d, J=15.0 Hz), 6.60(1H, s), 6.87(1H, s), 7.04(2H, brs), 7.40–7.80(4H, m), 8.23(1H, d, J=8.0 Hz), 9.40(1H, br)

The following compound was obtained by the procedure similar to that shown in the Example 35.

Sodium 7-[2-(2-thienyl)acetamide]-3-[2-(7-oxo-7H-thiopyrano[3,2-b]furan-5-yl)thiovinyl]-3-cephem-4-carbonate Melting Point: 175–180° C. (decomp.)

FAB-MS m/z: 555 [M+Na]$^+$

NMR(DMSO-d$_6$) δ: 3.50(2H, ABq, J=17.0 Hz), 3.80(2H, s), 5.05(1H, d, J=5.0 Hz), 5.55(1H, dd, J=5.0 Hz, 8.0 Hz), 6.45(1H, d, J=15.0 Hz), 6.95(2H, m), 7.05(1H, s), 7.17(1H, d, J=1.6 Hz), 7.35(1H, m), 7.55(1H, d, J=15.0 Hz), 8.24(1H, d, J=1.6 Hz), 9.10(1H, d, J=8.0 Hz)

Capability of Exploitation in Industry

The cephem compound according to the present invention has excellent antibacterial activity against MRSA and vancomycin-resistant *E. faecalis* and therefore is applicable to treatment of MRSA and other infections due to pathogenic bacteria.

What is claimed is:

1. A cephem compound or pharmaceutically acceptable salt thereof having the formula (I):

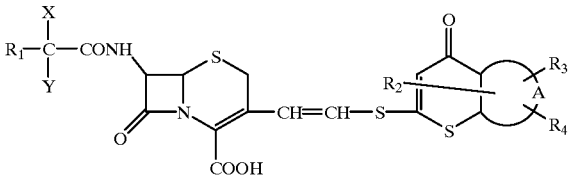

wherein

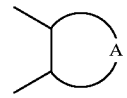

represents a benzene ring, pyridine ring, pyrazine ring, or a 5-membered aromatic heterocycle having one oxygen or sulfur atom as a ring-constituting atom;

X and Y each independently represents hydrogen or CXY represents C=N—OR$_5$, wherein R$_5$ represents hydrogen, halo C$_1$–C$_6$ alkyl or C$_3$–C$_7$ cycloalkyl;

R$_1$ represents phenyl, furyl, thienyl, thiazolyl which is optionally substituted, tetrazolyl or thiadiazolyl; and R$_2$, R$_3$ and R$_4$ each independently represents hydrogen, halogen, hydroxyl, nitro, C$_1$–C$_6$ alkoxy, trifluoromethyl, amino C$_1$–C$_6$ alkyl, halo C$_1$–C$_6$ alkyl, morpholino, piperidino or piperazinyl; with the proviso that when

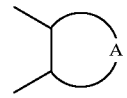

represents 5-membered aromatic heterocycle, no group R$_4$ is present.

2. The compound of claim 1, wherein

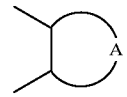

is a benzene ring.

3. The compound of claim 1, wherein

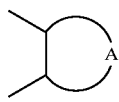

is a benzene ring; and X and Y each represent hydrogen.

4. The compound of claim 1, wherein

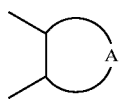

is a benzene ring; X and Y are each hydrogen; and $R_1$ is phenyl, thienyl or tetrazolyl.

5. The compound of claim 1 wherein

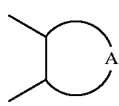

is a benzene ring; and CXY is C=N—$OR_5$, wherein $R_5$ is hydrogen, fluoromethyl or cyclopentyl.

6. The compound of claim 1, wherein

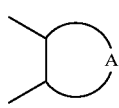

is a benzene ring; CXY is C=N—$OR_5$, wherein $R_5$ is hydrogen, fluoromethyl or cyclopentyl; and $R_1$ is amino-substituted thiazolyl.

7. The compound of claim 1, wherein

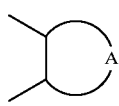

is a furan ring.

8. The compound of claim 1, wherein

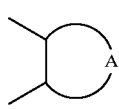

is a furan ring; CXY is C=N—OH; and $R_1$ is amino-substituted thiazolyl.

9. The compound of claim 1, wherein

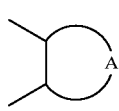

is a thiophene ring.

10. The compound of claim 1, wherein

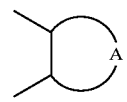

is a thiopene ring; X and Y are each hydrogen; and $R_1$ is thienyl.

11. The compound of claim 1, wherein

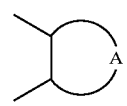

is a thiophene ring; CXY is C=N—OH; and $R_1$ is amino-substituted thiazolyl.

12. The compound of claim 1, wherein

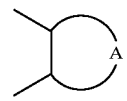

is a pyridine ring.

13. The compound of claim 1, wherein

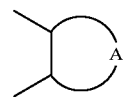

is a pyridine ring; X and Y are each hydrogen; and $R_1$ is thienyl.

14. The compound of claim 1, wherein

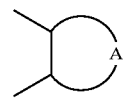

is a pyrazine ring.

15. The compound of claim 1, wherein

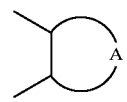

is a pyrazine ring; X and Y are each hydrogen; and $R_1$ is thienyl.

16. The compound of claim 1, which is a trans-isomer.

17. A compound having the formula (II):

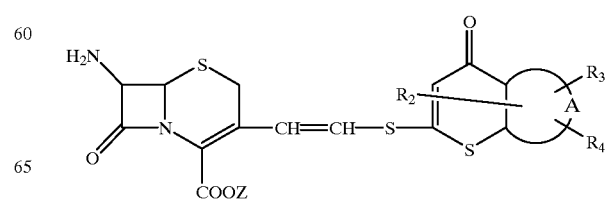

wherein

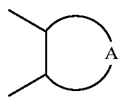

represents benzene ring, pyridine ring, pyrazine ring, or 5-membered aromatic heterocycle having one oxygen or sulfur atom as a ring-constituting atom; and $R_2$, $R_3$ and $R_4$ each independently represent hydrogen, halogen, hydroxyl, nitro, $C_1$–$C_6$ alkoxy, trifluoromethyl, halo $C_1$–$C_6$ alkyl, morpholino, piperidino or piperazinyl, and Z represents protective group for carbonyl.

18. The compound of claim 1, wherein CXY is an imino group of the formula C=N—$OR_5$, wherein $R_5$ is as defined, which is a syn isomer having the partial configuration:

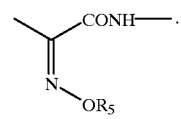

19. A pharmaceutical composition, comprising:

a) an effective amount of one or more of the compounds of claim 1; and b) a pharmaceutically acceptable carrier.

20. A method of treating a bacterial infection in a mammal, which comprises administering an effective amount of one or more compounds of claim 1, to a mammal in need thereof.

* * * * *